US006750200B1

(12) United States Patent
Tomich et al.

(10) Patent No.: US 6,750,200 B1
(45) Date of Patent: Jun. 15, 2004

(54) M2GLYR DERIVED CHANNEL FORMING PEPTIDES

(75) Inventors: John M. Tomich, Manhattan, KS (US); Takeo Iwamoto, Manhattan, KS (US); James R. Broughman, Manhattan, KS (US); Bruce D. Schultz, Wamego, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 09/710,419

(22) Filed: Nov. 9, 2000

(51) Int. Cl.[7] .......................... C12Q 1/00; C12N 15/00; G01N 27/416; C07K 7/00

(52) U.S. Cl. ......................... 514/13; 530/300; 530/326; 435/4; 435/325; 436/151; 514/14

(58) Field of Search ................................ 530/326, 300; 435/325, 4; 436/151; 514/13, 14

(56) References Cited

U.S. PATENT DOCUMENTS

| | | | |
|---|---|---|---|
| 5,368,712 | A | 11/1994 | Tomich et al. |
| 5,922,840 | A | 7/1999 | Tomich et al. |
| 6,077,826 | A | 6/2000 | Tomich et al. |

FOREIGN PATENT DOCUMENTS

| | | | |
|---|---|---|---|
| WO | WO 9726905 | * | 7/1997 |

OTHER PUBLICATIONS

Broughman, J.R., K. Mitchell, T. Iwamoto, B.D. Schultz, and J.M. Tomich. Amino–terminal Modification of a Channel–forming Peptide Increases Capacity for Epithelial Anion Secretion. *Am. J. Physiol*: (*Cell Physiol.*) (2000).

Esposito. G., B. Dhanapal, P. Dumy, V. Varma, M. Mutter, and G. Bodenhausen. Lysine as Helix C–capping Residue in a Synthetic Peptide. *Biopolymers* 41, 27–35 (1997).

Gao, L., J.R. Broughman, T. Iwamoto, J.M. Tomich, C.J> Venglarik, J.J. Forman, Synthetic Chloride Channel Restores Glutathione Secretion in Cystic Fibrosis Airway Epithelia. *Am. J. Physiol. Lung Cell Mol. Physiol.* 281:L24–L30, 2001.

Mitchell, K.E., J.M. Tomich, T. Iwamoto, and L.C. Freeman. A Synthetic Peptide Based on a Glycine–gated Chloride Channel Induces a Novel Chloride Conductance in Isolated Epithelial Cells. *Biochim. Biophys. Acta* 1466, 47–60 (2000).

Reddy, L.G., T. Iwamoto, J.M. Tomich, and M. Montal. Synthetic Peptides and Four–helix Bundle Proteins as Model Systems for the Pore–forming Structure of Channel Proteins. II. Transmembrane Segment M2 of the Brain Glycine Receptor Channel Is a Plausible Candidate for the Pore–lining Structure. *J. Biol. Chem.* 268, 14608–14615 (1993).

Tomich, J.M., D.P. Wallace, K. Henderson, R. Brandt, C.A. Ambler, A.J. Scott, K.E. Mitchell, G. Radke, J.J. Grantham. L.P. Sullivan, and T. Iwamoto. Aqueous Solubilization of Transmembrane Peptide Sequences with Retention of Membrane insertion and Function. *Biopys J.* 74, 256–267 (1998).

Tomich, J.M. Amphipathic Helices in Channel–Forming Structures. *The Amphipathic Helix* Chap. 9, pp. 221–254 (1993).

Wallace, D.P., J.M. Tomich, T. Iwamoto, K. Henderson, J.J. Grantham, and L.P. Sullivan. A Synthetic Peptide Derived from teh Glycine–gated Cl–channel Generates Cl–channel Induces transepithelial Cl– and fluid secretion by Epithelial Monolayers. *Am. J. Physiol*: 272 (*Cell Physiol.* 41) C1672–C1679 (1997).

Wallace, D.P., J.M. Tomich, J. Eppler, T. Iwamoto, J.J. Grantham, and L.P. Sullivan, A Synthetic Channel–Forming Peptide Induces Cl– Secretion: Modulation by $Ca^{2+}$–dependent $K^+$ Channels. *Biochim. Biophys. Acta* 1464, 69–82 (2000).

* cited by examiner

*Primary Examiner*—Lorraine Spector
*Assistant Examiner*—Joseph F. Murphy
(74) *Attorney, Agent, or Firm*—Hovey Williams LLP

(57) ABSTRACT

The present invention provides a family of peptides based upon the M2GlyR sequence. These peptides are derivatives of the M2GlyR sequence and can be modified at their ends to include a plurality of polar amino acid residues to enhance their solubility. Particularly preferred derivatives include portions of the M2GlyR sequence which are palindromic to another portion of the peptide or to the M2GlyR sequence itself. Preferably these portions are at least 7 amino acid residues in length. Peptides embraced by the present invention are characterized by having greater effects on the transepithelial electrical resistance of cells at lower concentrations. Peptides of the present invention have been shown to increase Isc in MDCK epithelial cell monolayers with half maximal effects observed at or below 30 μM, a nearly 10-fold improvement over any peptide previously characterized in the M2GlyR family.

1 Claim, 15 Drawing Sheets

Effects of M2GlyR Modified Sequences on $I_{sc}$ in MDCK Monolayers

SEQ ID No. 34
NK4-p22

$I_{sc}$ in MDCK cell monolayers.
E = 1-EBIO; all numbers represent μM concentrations.
Dotted line is at zero μA.

SEQ ID No. 19
CK4(A-L-a)

$I_{sc}$ in MDCK cell monolayers.
E = 1-EBIO; all numbers represent μM concentrations.
Dotted line is at zero μA.

Effects of M2GlyR Modified Sequences on $I_{sc}$ in MDCK Monolayers

SEQ ID No. 9
NK4(A'-W-a')

$I_{sc}$ in MDCK cell monolayers.
E = 1-EBIO; all numbers represent µM concentrations..
Dotted line is at zero µA.

SEQ ID No. 27
NK4(A'-L-a')

$I_{sc}$ in MDCK cell monolayers.
E = 1-EBIO; all numbers represent µM concentrations.
Dotted line is at zero µA.

Effects of M2GlyR Modified Sequences on $I_{sc}$ in MDCK Monolayers

SEQ ID No. 5
NK4(a-L-a')

$I_{sc}$ in MDCK cell monolayers.
E = 1-EBIO; all numbers represent μM concentrations.
Dotted line is at zero μA.

Computer Models of C- and N-$K_4$ A•L•a

Computer Model of N-$K_4$ A•L•a

TOCSY Fingerprint Regions of C-$K_4$ A•L•a
SEQ ID No. 19

TOCSY Fingerprint Regions of N-$K_4$ A L•a
SEQ ID No. 18

Representative Circular Dichroism Spectra for M2GlyR Variants
$[\theta] = deg\ dmol^{-1}\ cm^2$ SEQ ID No. 26

Representative Circular Dichroism Spectra for M2GlyR Variants
$[\theta] = deg\ dmol^{-1}\ cm^2$ SEQ ID No. 5

Representative Circular Dichroism Spectra for M2GlyR Variants $[\theta] = deg\ dmol^{-1}\ cm^2$ SEQ ID No. 19

Fluorescence Emission Properties of SEQ ID No. 9 in Buffer and 1mM Liposome Solution Fluorescence Emission Properties of SEQ ID No. 9 in Buffer and 1mM Liposome Solution Cross-Linking Experiment SEQ ID No. 3
N-$K_4$ M2GlyR in water SEQ ID No. 2
C-$K_4$ M2GlyR in water Cross-Linking Experiment SEQ ID No. 3
N-$K_4$ M2GlyR
(KKKKPARVGLGITTVLTMTTQSSGSRA)

SEQ ID No. 18
N-$K_4$ A•L•a
(KKKKAARVGLGITTVLVTTIGLGVRAA)

Concentration Dependence of Cross-Linking

Concentration Dependence of Cross-Linking SEQ ID No. 9
NK4-A'Wa'

M2GLYR DERIVED CHANNEL FORMING PEPTIDES

FEDERALLY SPONSORED RESEARCH OR DEVELOPMENT

This invention was made with government support under Grant GM43617 awarded by the National Institutes of Health. The government has certain rights in the invention.

SEQUENCE LISTING

A printed Sequence Listing accompanies this application, and has also been submitted with identical contents in the form of a computer-readable ASCII file on a floppy diskette.

BACKGROUND OF THE INVENTION

1. Field of the Invention

The present invention is broadly concerned with multiple-peptide channel assemblies which provide transport of anions through epithelial cell membranes wherein the preferred peptides have from about 16–31 amino acid residues and are soluble in water to a level of at least 5 mM; such channel assemblies can be used in the treatment of diseases such as cystic fibrosis (CF) and adult polycystic kidney disease (APKD), as well as in the killing of undesirable cells. More particularly, the invention pertains to such channel assembly forming peptides, and corresponding methods of use, wherein the peptides are derived from a segment of a native (i.e., naturally occurring) channel protein and have their water solubilities enhanced by modification of the C- or N-ends thereof modified with a plurality of polar amino acid residues such as lysine. Still more particularly, the invention pertains to derivatives of the M2GlyR sequence which remain predominantly in monomer form when in solution, have a desired amount of helical configuration, and alter the transepithelial electrical resistance of cells to a greater extent than was heretofore possible.

2. Description of the Prior Art

Introduction.

A major problem in CF is the inability of airway epithelia to secrete fluid. The resulting changes in the composition of the mucous coating the airway epithelia result in infection and subsequent inflammation, scarring, and eventual pulmonary destruction. The basis of the problem is the absence of functional cystic fibrosis transmembrane conductance regulator (CFTR) in the apical membrane of the epithelial cells. This leads to an increase in the absorption of salt and water and an inability to respond to appropriate stimuli by secreting chloride and water. CFTR is a chloride channel; in addition it down-regulates sodium channels and up-regulates another population of chloride channels, the outwardly rectifying chloride channel (ORCC). These properties of CFTR enable the airway cells to secrete chloride and this drives the secretion of sodium and water.

A synthetic-23-residue α-helical peptide designated M2GlyR forms anion-selective channels in phospholipid bilayers. This peptide has the amino acid sequence of the putative transmembrane segment M2 of the strychnine-binding a subunit of the inhibitory glycine receptor.

The origin and properties of M2GlyR.

The glycine receptor is a membrane protein present in post-synaptic membranes. Binding of glycine activates a $Cl^-$ conducting channel, leading to hyperpolarization of the membrane and inhibition of the synapse. The receptor consists of two major glyco-polypeptides, an a subunit of 48 kd and a β subunit of 58 kd, and a receptor-associated cytoplasmic protein of 93 kd. Strychnine, an antagonist of the glycine receptor, binds only to the α subunit. Messenger RNA corresponding to this subunit leads to the expression of functional, glycine-activated, $Cl^-$ channels upon injection into Xenopus oocytes.

The glycine receptor channel in cultures of embryonic mouse spinal cord is selective for monovalent anions, with conductances of 27 and 46 pS in 145 mM $Cl^-$ solution. Pharmacological studies suggested the presence of two sequentially occupied anion binding sites in the channel. These sites are considered to be the functional correlates of the positively charged amino acids bordering the M2 segment of the α subunits. This finding led to the development of the synthetic peptide with the sequence of the M2 segment of the glycine receptor.

Electrical recordings from phospholipid bilayers containing M2GlyR showed single-channel conductances of 25 pS and 49 pS in symmetric 0.5 M KCl with channel open lifetimes in the millisecond range. Single channel events occurred in 0.5 M N-methyl-D-glucamine HCl but not in sodium gluconate, indicating that the channel is anion selective. A transference number for anions of 0.85 was calculated from reversal potential measurements under a 5-fold KCl concentration gradient.

After insertion into the lipid bilayers the monomeric peptides self-assemble to form conductive oligomers of different amplitudes. To gain control over the aggregate number, four identical M2GlyR peptide units were tethered to a 9-amino acid carrier template to form a four-helix bundle protein. This tetramer, incorporated into lipid bilayers, formed channels of uniform unitary conductance of 25 pS. The 49 pS conductance described above is presumed to be due to the presence of a pentamer.

The tetrameric channel was blocked by the $Cl^-$ channel blockers 9-anthracene carboxylic acid (9-AC) and niflumic acid (NFA). It was not blocked by QX-222, an analogue of lidocaine and a blocker of cation-selective channels. Strychnine, an antagonist of the glycine receptor, does not block the channel-forming tetramer. Strychnine is presumed to bind to the ligand-binding domain of the receptor exposed to the extracellular surface but not to the channel domain.

Structure of channel forming peptides.

While great strides have been made in the area of channel function and regulation, using the intact protein or in some cases purified channel proteins reconstituted into model membranes, many aspects of channel function remain unresolved. The $K^+$ from streptomyces lividans was crystallized and the structure determined at 3.2 Angstroms. This structure has served as a model for other related channels using homology modeling methodologies. This structure however is for a 4 subunit channel as opposed the five subunit channel proposed for the glycine receptor.

Considerable structural data exists for the related class of channel forming peptides (CFPs). These channels are much smaller in size and contain only a ring of short peptide chains organized around the central ion conducting pore in the lipid bilayer. These channels are unique in that they assemble by the oligomerization of a single peptide. These structures are models for studying the structure and function of the various regulated channels that occur in nature. This class of CFPs includes: the α-aminoisobutyric acid-containing channels such as alamethicin and zervamicin, and a number of toxins and venoms such as melittin, cecropins, mast cell degranulating peptides, and the defensins. Melittin is somewhat of a special case because it forms channels only at low concentrations; at higher concentrations it acts as a lytic agent. In some cases CFPs assemble spontaneously upon insertion into the bilayer while in the remaining cases the assembly requires an electrical potential across the membrane ($V_m$).

The structure of the channels arising from the assembly of these peptides vary from trimers to hexadecamers associated in the form of helical bundles or β-barrels. The most widely accepted model which is in accord with the model for channel proteins has the helices arranged with their dipoles all pointing in the same direction (parallel). Since CFP channels, unlike authentic channel proteins, are not generated from the association of large protein subunits, alternative stabilization schemes must be invoked to account for the presence of this higher energy arrangement of parallel segments. These could include aligning the dipoles in response to the presence of the membrane potential and/or an increase in the favorable inter-molecular interactions promoted by the parallel assembly. Most CFPs form multiple size bundles of parallel segments (e.g., n=4, 5, 6) that can spontaneously increase or decrease in size upon the addition or deletion of a peptide monomer from the channel assembly. These observations imply that enough information is contained in a single channel forming polypeptide to drive the correct folding, assembly, and activity of these channels.

The activity of these assembled molecules, the opening and closing of the channels on the millisecond time scale, has been ascribed to numerous effects. Three different helical motions have been implicated: the bending and twisting of the helices, rigid-body fluctuations of the entire assembled structure with the lipid bilayer, and rotational motions of the polypeptide around its helical axis. Another hypothesis suggests that channel activity is a consequence of a conformational change that is transmitted along the helical axis. Others suggest that the movement of individual amino acid side-chains could provide this function, and one group contends that an electron transfer could disrupt a hydrogen bonding of four tyrosines in $K^+$ channels.

Fluorescence, Fourier transform infrared spectroscopy (FTIR), and circular dichroism (CD) measured in organic solvents, phospholipid micelles, liposomes, or oriented phospholipid bilayers, have been successfully used to probe the solution and membrane-bound conformations of these peptides. Computer modeling studies have been performed to estimate the energetics of moving a charged ion across a lipid bilayer through a pore generated by a bundle of transmembrane helices. Structural experiments using NMR are yielding important results. In general, these studies have provided several conclusions concerning the solution behavior and membrane interactions of CFPs. Amphipathic helical peptides can exist as monomers and aggregates in solution. Monomers are able to interact much more readily with lipid bilayers and micelles. Depending on the peptide to lipid ratios, type of lipid, ionic strength, pH of the solution, and the hydration of the lipid, the peptide will preferentially orient itself either parallel to or perpendicular to the plane of the bilayer. Many CFPs do not require a potential difference across the bilayer to insert spontaneously into the bilayer. Once in the membrane, the helices associate in a time and concentration dependent manner to form the multistate helical bundles. It is these assemblies that conduct the ions across the bilayer. These studies, when considered together, reveal the transmembrane amphipathic helix to be a dynamic structure. The ability to oligomerize in the membrane into stable ring structures, with a central aqueous pore capable of opening and closing, appears to be driven by the asymmetric alignment of hydrophilic and hydrophobic amino acid residues that seem to obey a unique set of rules.

Putative channel forming segments from large channel proteins behave much like the small naturally occurring CFPs described above. They spontaneously insert into bilayers and self-assemble into an ion-conducting structure, presumably comprised of a parallel array of α-helices. These structures also retain biological activities reminiscent of the native proteins they were modeled after. These structures are reasonable models for exploring both the oligomerization of transmembrane segments and for defining the molecular events that give rise to channel activity. The beauty of this system emanates from the appearance of a measurable activity that arises from the assembly of an amphipathic transmembrane helix. The activity allows measurement of the effects of amino acid substitutions on either the size of the assemblies or the contribution of the residues to ion selectivity or translocation. The number of helices per channel can be precisely controlled, thus preventing multiple oligomerization states, by tethering the helical segments to a peptide backbone during synthesis. The small size of these assemblies makes them ideally suited for NMR structural studies using either detergent micelle solution NMR or oriented bilayer solid-state NMR.

Pharmacological studies have been a relatively recent addition to the single channel analysis of these model CFP channels. Using a four helix bundle CFP derived from the human L-type dihydropyridine sensitive $Ca^{2+}$ channel, the binding of a local anaesthetic as well as a number of calcium channel blockers with binding affinities on the order of those observed for the full length calcium channel protein have been observed. This avenue of investigation adds a sensitive method of discriminating between channels that truly mimic their parent structures as opposed to those that might produce non-discriminating ionic pores. Once the three dimensional structure for one of the synthetic channels has been solved, rational drug design of both channel agonists and antagonists may be attempted using these coordinates.

Membrane proteins are generally acknowledged to be the most difficult class of proteins for detailed structural analysis. The studies presented above clearly demonstrate the utility of working with channel forming peptides, as model systems, to study events involved in peptide association with the bilayer, insertion into membranes, and assembly into oligomers. The amphipathic helix is a suitable structural motif for the pore of channel proteins that also contributes to the organization, size, function, and stabilization of ionic channels. As an assembled structure these helical bundles can be used to investigate the structure, organization, and function of channels.

Application of synthetic peptides to biological membranes.

A synthetic peptide with the sequence of the M2δ segment of the nicotinic acetylcholine receptor from *Torpedo californica* forms ion channels in lipid bilayers that emulate those of authentic acetylcholine receptor ion channels. Human erthyrocytes exposed to the synthetic peptide released hemoglobin and $K^+$. Evidently the peptide molecules self-assembled in the membrane to form trimers and pentamers. Extensive evidence indicates that $Cl^-$ secretion drives fluid secretion in Madin-Darby canine kidney (MDCK) cells and in cells cultured from the cystic epithelium of the kidneys of patients with autosomal dominant polycystic kidney disease (APKD), and that a $Cl^-$ channel is involved in fluid secretion. Indeed there is now extensive data indicating that CFTR is the channel involved in that secretion by APKD cells. Apparently, a net secretion of $Cl^-$ into the lumen of the cysts leads to an increase in water volume in the cysts, ultimately resulting in kidney dysfunction. However, although there is a precedent for the application of synthetic channel-forming peptides to cells, no one previously has used channel-forming peptides to treat symptoms of any disease.

U.S. Pat. No. 5,543,399 describes the purification and lipid reconstitution of CFTR protein and CF therapy making use of that protein. There is no teaching or suggestion in this reference of the use of relatively small, easily prepared pure peptides, and particularly peptides which are fragments of channel-forming proteins.

U.S. Pat. No. 5,368,712 teaches the use of small peptides reconstituted in artificial membranes as diagnostic tools. This patent does not describe any therapeutic applications using such peptides.

U.S. Pat. No. 6,077,826, the content of which is hereby incorporated by reference, describes the use of multiple-peptide channel assemblies which transport anions through epithelial cells, synthetic peptides capable of forming such assemblies, channel assemblies which alter the flux of water across these cells, and channel assemblies which alter the transepithelial electrical resistance of cells. These assemblies were based on the M2GlyR sequence and were modified to increase their solubility. However, the activity of these assemblies is limited to about 15 $\mu A/cm^2$ at a concentration of about 500 $\mu M$. Additionally, the peptides of this invention form multimers in solution which have decreased affinity for membranes and suffer from solution aggregation.

Accordingly, what is needed in the art are channel assemblies which exhibit a more potent effect on the transepithelial electrical resistance of cells and transport anions through cells with a greater efficiency. Such peptides should also exhibit greater stability and a lower occurrence of multimers when added to solution.

SUMMARY OF THE INVENTION

The present invention solves the problems inherent in the prior art and provides a distinct advance in the state of the art. Peptides of the present invention exhibit an improvement in activity that is about 5 fold greater with respect to activity levels and/or a 10 fold increase in effective concentration than was heretofore possible. The present invention is directed to improved 1) multiple peptide channel assemblies for transport of anions (e.g., $Cl^-$) through epithelial cells, 2) synthetic peptides capable of forming such channel assemblies, 3) methods of using the channel assemblies in therapeutic contexts for altering the flux of water across epithelial cells, and 4) multiple peptide channel assemblies which alter the transepithelial electrical resistance of cells. The peptides of present invention exhibit greater stability and reduced solution aggregation which lead to increased bio-availability of the peptides, thereby reducing the amount of peptide necessary to affect a desired response. Additionally, the present invention is directed to peptide sequences which can form channel assemblies having unique cell-killing attributes and which may be useful in combating growth of undesirable cells (e.g. cancer cells).

In preferred forms, the channel assemblies of the invention comprise multiple peptides each having from about 16–31 amino acid residues, and more preferably from about 22–27 residues. The peptides are characterized by the ability of providing, in an embedded channel assembly, transport of anions through a membrane of an epithelial cell and modulation (alteration) of the flux of water through the cell. The peptides are also characterized by their effect on the transepithelial electrical resistance of cell monolayers. Preferred peptides of the present invention will have activity profiles of greater than about 15.0 $\mu A/cm^2$ in MDCK cells when applied to the MDCK cells at a concentration of about 500 $\mu M$. More preferably, peptides of the present invention will have activity profiles of greater than about 15.0 $\mu A/cm^2$ in MDCK cells when applied to the MDCK cells at a concentration of about 300 $\mu M$, and still more preferably at a concentration of about 200 $\mu M$, and most preferably at a concnetration of less than about 100 $\mu M$. Moreover, the preferred peptides are soluble in water to a level of at least about 5 mM, and more preferably at least about 10 mM, and still more preferably at least about 15 mM. The peptides of the invention also should exhibit at least about 50% helical content (advantageously at least about 65% helical content, and still more preferably at least about 75%) when dispersed in a 20% trifluoroethanol/80% water solution and measured using circular dichroism spectroscopy (CD). Preferred peptides of the present invention are also characterized by greater stability and fewer multimeric forms in solutions. Preferably, the peptides will predominantly form only monomers when dissolved in solution, with just a trace of dimer present. Monomers are preferred due to their higher binding affinity to the membrane. This increased affinity is due to the non-aggregation of the hydrophobic portions which are required for membrane binding, and are therefore available for binding. This increases the overall bio-availability of sequences comprising mainly monomers. When sequences include multimeric forms, the hydrophobic portions aggregate, thereby rendering them unavailable for binding and decreasing their bio-availability. For peptide sequences having cell-killing attributes, such sequences will induce a negative effect on the resistivity of cell monolayers, eventually leading to a breakdown of the monolayers and the death of the cell. This negative effect is thought to break down the junctions between cell layers. However, this effect is not seen when isolated cells are exposed to these peptide sequences.

In the case of CF therapies, the channel assemblies are embedded in the cytoplasmic membrane of affected epithelial cells. These peptides spontaneously insert into the cytoplasmic membrane on contact, and spontaneously aggregate within the membrane to form a channel assembly having a hydrophilic internal pore through which $Cl^-$ may pass, and an lipophilic external surface allowing solubility of the assembly in the membrane. Preferably, the peptides making up the channel assemblies are identical. In another use, the peptides may spontaneously insert into the basolateral membrane of renal epithelial cells in order to inhibit the flux of water into the adjacent cysts.

The peptides ideally have an amino acid sequence based upon the sequence of the M2GlyR peptide which has been subsequently modified by the addition of multiple polar amino acid residues on the C- or N-ends. C-$K_4$-M2GlyR (PARVGLGITTVL-TMTTQSSGSRAKKKK)(SEQ ID No. 2), was initially chosen as the lead CF drug compound due to its higher solubility in water, higher proportion of monomer in solution, and its ability to better mimic the pharmacology associated with the unmodified M2GlyR sequence. The second peptide N-$K_4$-M2GlyR (SEQ ID No. 3) (KKKKPARVGLGITTVLTM-TTQSSGSRA), upon closer analysis, shows an approximately 50% higher level of conductance than the C-$K_4$ peptide. It also appeared to form channels faster and had channels with improved stability. This increase in activity may be due to a structural difference that was been observed in modeling studies. In addition to these differences, other disparate properties such as degrees of aggregation in solution, rates of aggregation in physiological buffers and sensitivities to different channel blocking agents have been noted between the two peptides. These artificial anion conducting channels appear to be regulated by potassium channels located in the baso-lateral membrane. The anion conductance seen with C-$K_4$-M2GlyR, is most likely, the result of a novel chloride conductance pathway. These measurements were obtained using Madin-Darby canine kidney cells, the human colonic epithelial cell line (T84), and airway epithelial cells derived from a human cystic fibrosis patient (IB3-1). N-$K_4$-M2GlyR also acts to form a novel chloride conductance pathway but yields an approximately 50% increase in short circuit current (Isc) over that of C-$K_4$-M2GlyR as described above. This increase in activity may be due to a structural difference that has been observed in modeling studies. In recent studies, both peptides were shown to restore glutathione transport in cultured CF monolayers. Again, C-$K_4$-M2GlyR was active but to a much lesser extent, thereby reaffirming the theory that N-$K_4$-M2GlyR functions better than C-$K_4$-M2GlyR. The fact that N-$K_4$-M2GlyR can be regulated by the cell through baso-lateral K+ channels and that its presence in compromised CF cell line helps restore glutathione transport, suggests that this peptide improves the health of CF cells.

However, one of the obstacles to generating better channel forming sequences based on the M2GlyR sequence has been the multi-state nature of N-$K_4$M2GlyR and C-$K_4$M2GlyR in solution. Therefore, in an attempt to reduce the amount of solution aggregation, a new family of peptides based on the M2GlyR sequence was created using a modular approach. The modules consist of the 11 amino acid residue segments surround the central leucine (L) residue: module A=PARVGLGITTV (SEQ ID No. 48) and module B=TMTTQSSGSRA (SEQ ID No. 49). Using this nomenclature, the native sequence for M2GlyR is A.L.B. Derivative sequences were created using module A (PARVGLGITTV), module B (TMTTQSSGSRA), the A module in reverse (VTTIGLGVRAP) (SEQ ID No. 50), referred to as a, the B module in reverse (ARSGSSQTTMT) (SEQ ID No. 51) referred to as b, A' (AARVGLGITTV) (SEQ ID No. 52) having an alanine substituted for the initial proline, and a' (VTTIGLGVRAA) (SEQ ID No. 53) which is the A' module in reverse. New sequences were generated by combining the six modules, A, B, a, b, A', and a', in all possible combinations separated by the leucine normally found between these modules in the wild-type sequence. Sequences such as A.L.A, a.L.a, a.L.A, A'.L.b, etc. were synthesized. In other sequences comprising the six modules, tryptophan (W) was used between the modules, as opposed to the naturally occurring leucine.

Preliminary results indicated those newly designed peptides with a propensity to form an alpha-helical structure (assessed by CD in 20% trifluoroethanol (TFE) in $H_2O$), were more likely to promote anion secretion across epithelial cell monolayers. For peptides which have an activity less than 1, such peptides generally have less than 20% helicity and exhibit a structure more closely related to a beta structure, which has difficulty forming pores in membranes. For peptides having activities greater than 1, such peptides generally have greater than 20% helicity which helps form the bundle and thereby, form a pore through a membrane.

Based upon success in solubilizing transmembrane sequences, amino-terminal lysyl adducts were added to the C- and N-termini of the new modular mutants. C- and N-$K_4$-(A.L.a) (PARVGLGITTV-L-VTTIGLGVRAP) exhibited higher activity than had previously been found in the prior art. Because this sequence is a palindrome, the amino- and carboxyl-terminal lysyl adducts allow for testing the effects of the helical dipole on anion transport. Both adducts have shown increased Isc in MDCK epithelial cell monolayers with half maximal effects observed at or below 30 $\mu$M, a nearly 10-fold improvement over any peptide previously characterized in the C- and N-$K_4$ M2GlyR family. C-$K_4$ A.l.a, however, produced channels that were toxic to the cell while N-$K_4$ A.l.a produced equally high conductance levels (up to 45 $\mu$Amp/cm$^2$) that were not harmful to isolated cells. SDS-PAGE gels of cross-link ed peptide revealed that the N-$K_4$ A.l.a is>90% monomeric with only a trace of dimer and nothing higher.

Computer modeling studies were subsequently performed on many of the known active sequence-using conditions that mimicked folding in the membrane phase (low dielectric). Under these conditions an unexpected result was obtained. The structure for C-$K_4$ M2GlyR as well as the palindrome C-$K_4$ A.L.a had the four lysine residues folded back at the C-terminus. Hydrogen bonds were formed between two of these lysine residues and the helix backbone. In contrast, the lysine residues at the N-terminus of the palindromic sequence C-$K_4$ A.L.a extended away from the helix and were not H-bonded. These preliminary results were consistent with the results obtained from the C-capping of a synthetic peptide modified with a single lysine at the C-terminus determined from NMR. The C-capped structures also showed a moderate compression in the second turn of the helix at the amino terminus. The implications of this structure on function are significant for transmembrane sequences. In designing the water soluble N-$K_4$ and C-$K_4$ derivatives, it was assumed that the lysine residues would be solvent exposed and also serve to restrict the membrane insertion of the peptides to only one orientation with the lysines remaining outside the membrane. Having the lysines at either terminus should have allowed for the insertion of the peptide with its helix dipole oriented exclusively in one direction. Therefore any assemblage of the inserted sequences should be the result of bundles of parallel helices.

However based on the computer models, the predicted folding back of the lysines in the case of C-$K_4$ M2GlyR suggested that both orientations of the peptide were possible. Most models of the assembled pores formed by channel forming peptides have all helical dipoles parallel. In the case of C-$K_4$ M2GlyR having both orientations of the dipole possible within the membrane would interfere with the assembly of an active synthetic channel. Early modeling studies on M2 have suggested that anti-parallel packing of the helices leads to an assembly without a central pore. Thus, it is likely that an anti-parallel bundle of C-$K_4$ M2GlyR peptides would be non-functional. Before the possibility of multiple orientations within the membrane for C-$K_4$ was recognized, the working hypothesis was that the higher the concentration of monomer (in solution), gave rise to higher activity in cells. Now it appears that one must also consider (in the case of C-$K_4$ peptides) the concentration of peptide in the membrane with the correct orientation of dipoles as well as the competitive inhibition that might arise from complexation of helices with the opposite dipole.

Physical data from other experiments support the modeling data described above. In a set of cross-linking experiments designed to characterize aggregates of the two sequences in water, N-$K_4$ M2GlyR gave a ladder of bands starting from monomer up to assemblies approaching 36 kDa. However, C-$K_4$ M2GlyR showed only trace amounts of aggregates higher than trimer. Assuming that the lysines are participating in hydrogen bonds with the backbone carbonyls, two postulates can be proposed; 1) the lysine ϵ-amino groups are not readily available for cross-linking or 2) the lysine C-capping disrupts the ability to form the pores in membranes or form aggregates in solution.

A series of single and multi-dimensional NMR experiments were performed on the modular mutants N- and C-$K_4$ A.L.a. Preliminary NMR data on N-$K_4$ A.L.a and C$K_4$-A.L.a shows the fingerprint region (NH to Ca and side chain proton connectivity) of 1H-1H 2D-TOCSY NMR spectra of these peptides recorded in water containing 30% deuterated TFE at 30° C. These spectra displayed reasonably sharp lines and the chemical shift dispersion. The upfield shifting of lysine backbone amide protons and down field shifting of side chain NH cross peaks in TOCSY spectra of C-$K_4$-A.L.a in comparison to N-$K_4$-A.L.a clearly indicate that in the C$K_4$ variant, the lysine backbone amine hydrogen might be hydrogen-bonded and side chains folded whereas in N$K_4$ variants, the lysine residues are in extended conformation.

It has also been demonstrated that NMR is a very sensitive technique for assessing the degree of aggregation for soluble peptides based on the M2 transmembrane segment of the brain glycine receptor (M2GlyR), thereby allowing the formulation of the hypothesis that an increase in monomers leads to higher activity. These new initial results indicate that proposed transmembrane peptides have conformational and topographical properties which are observable by NMR spectroscopy and this information confirms the current computer models.

Initially, the most active variant form of M2 was SEQ ID No. 18. Several modifications were made to this sequence and subsequently tested. Some of these variants have enhanced activity in comparison to SEQ ID No. 18. This enhanced activity is present despite the fact that variants of M2GlyR tested included palindromic sequences, mutated sequences, deleted sequences, and combinations of all of these. Some sequences included replacements for one or both proline residues as well as deletion or additions of the central leucine residue(s). Removal of the prolines improves the ease of synthesis and the deletion or addition of leucines has the effect of changing the registry of the lower C-terminal portion of the helix. By removing the central leucine, the lower cylinder of the helix is rotated −100°. The addition of two three, and four leucines have the effect of rotating the helix +100°, +200° and +300°, respectively. These changes are required to see if helical packing within the assembly bundles can be altered and make a better behaved pore structure. It is presumed that these sequences having additional leucines will also exhibit an effect on transepithelial electrical resistance of cells.

In another approach, a series of deletion peptides were prepared for both N-$K_4$ M2GlyR and C-$K_4$ M2GlyR. In each case, amino acid residues were deleted from the end opposite the lysine tail. These peptides were designed to test the lengths of the peptides, both N- and C-$K_4$ M2GlyR, that would sustain bio-activity. Additionally, peptides that had amino acid residues deleted from the end opposite the oligo-lysyl tail were prepared and tested.

It is quite apparent from the activity profiles for these sequences that the N-$K_4$ series retains high activity ($\mu$A/cm$^2$) over a larger range of peptide lengths than do the C-$K_4$ sequences. Knowing the minimal length sequence that retains full activity could save resources in both the synthesis and subsequent purification of the active sequence. The N-$K_4$ series dropped significantly after 5 residues were deleted. The C-$K_4$ truncated peptides began to lose significant activity with the first deletion. However, activity in many of these truncated peptides remained higher than that determined for either N- or C-$K_4$-M2GlyR. Based on this model, N-$K_4$ p25 and p22 maintain full activity by recruiting the extended lysyl terminus. For these shorter species, the long hydrophobic butyl side chains of lysine allow the ϵ-amino groups to remain within the charged phospholipid headgroup region of the bilayer as the entire helix retains its ability to fully span the bilayer by being pulled down into the membrane. In the case of the C-$K_4$ truncated peptides the lysines are unavailable for this function due to their folded-back conformation and therefore, the peptides begin to lose their ability to fully span the membrane after truncation.

One somewhat unrelated peptide was also generated and tested. SEQ ID No. 47 represents a double ended version of the M2GlyR peptide in that four lysine residues have been added to both ends of the peptide. It was postulated that this sequence would also work since the lysine residues located at the C-terminus are involved in hydrogen bonds. As described above, this C-capping phenomenon should reduce the net charge of the C-terminus and allow it to enter into the bilayer and cross to the other side. Experimental evidence suggests that the peptide induces only about 5 $\mu$A/cm$^2$ acitivity but upon protease cleavage yields about 20 $\mu$A/cm$^2$.

The present invention also includes a method of altering the flux of water from an epithelial cell presenting first and second spaced apart surfaces. The method broadly includes providing multiple peptides capable of forming a channel assembly with each of such peptides having from about 16–31 amino acid residues therein. These peptides are contacted with the first surface of an epithelial cell thereby causing the peptides to embed therein and alter the flux of water across the cell. In accordance with the method aspects of the invention, the epithelial cells may be selected from the group consisting of CF-affected epithelial cells, e.g., cells selected from the group consisting of airway, intestinal, pancreatic duct and epidymus epithelial cells. In the case of airway epithelial cells, the method further comprises a delivery step immediately preceding the contacting step, wherein the channel-forming peptides are aerosolized inhaled. In another representative method, the epithelial cells are cystic epithelium of an APKD-affected individual, and the first surface of the epithelial cells is the basolateral membrane of such cells.

In another method of the present invention, the resistivity of cell layers can be decreased by contacting the cell layer with a peptide. Preferably, the peptide is a derivative of SEQ ID No. 1 and includes a portion which is palindromic to a portion of SEQ ID No. 1 or to itself. Preferably, this palindromic portion comprises at least about 7 amino acid residues, more preferably at least about 9 amino acid residues and still more preferably, at least about 11 amino acid residues. In order to increase the solubility of these peptides, the C- and/or N-terminuses thereof can be modified to contain a plurality of polar amino acids thereon. A particularly preferred polar amino acid is lysine. The concentration of the peptide necessary for decreasing the cell layer resistivity is preferably up to about 500 $\mu$M, more preferably up to about 300 $\mu$M, still more preferably up to about 200 $\mu$M, and most preferably, less than about 100 $\mu$M. Particularly preferred peptides will have at least about 35% sequence homology with a sequence selected from the group consisting of SEQ ID Nos. 4–47. More preferably, these peptides will have at least about 50% sequence homology (and most preferably at least about 65% sequence homology) with a peptide selected from the group consisting of SEQ ID Nos. 4–47.

The channel-forming peptides of the invention are normally in the L-stereoconfiguration. However, the invention is not so limited and indeed D-stereoconfiguration peptides can also be used. The latter type of peptides may also have significant advantages as they are not degraded in vivo by proteolytic enzymes nor do they elicit an immune response.

As used herein, the following definitions will apply: "Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol.,215:403–410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403–410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 95% "sequence identity" to a reference nucleotide sequence, it is intended that the nucleotide sequence of the given polynucleotide is identical to the reference sequence except that the given polynucleotide sequence may include up to 5 point mutations per each 100 nucleotides of the reference nucleotide sequence. In other words, in a polynucleotide having a nucleotide sequence having at least 95% identity relative to the reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 95% sequence identity to a reference amino acid sequence, it is intended that the given amino acid sequence of the polypeptide is identical to the reference sequence except that the given polypeptide sequence may include up to 5 amino acid alterations per each 100 amino acids of the reference amino acid sequence. In other words, to obtain a given polypeptide sequence having at least 95% sequence identity with a reference amino acid sequence, up to 5% of the amino acid residues in the reference sequence may be deleted or substituted with another amino acid, or a number of amino acids up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

Similarly, "sequence homology", as used herein, also refers to a method of determining the relatedness of two sequences. To determine sequence homology, two or more sequences are optimally aligned as described above, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 95% of the amino acid residues or nucleotides in the reference sequence must match or comprise a conservative substitution with another amino acid or nucleotide, or a number of amino acids or nucleotides up to 5% of the total amino acid residues or nucleotides, not including conservative substitutions, in the reference sequence may be inserted into the reference sequence.

A "conservative substitution" refers to the substitution of an amino acid residue or nucleotide with another amino acid residue or nucleotide having similar characteristics or properties including size, hydrophobicity, etc., such that the overall functionality does not change significantly.

"Isolated" means altered "by the hand of man" from its natural state., i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

As used herein, "derivative" with respect to M2GlyR, refers to mutants produced by amino acid addition, deletion, replacement, and/or modification; mutants produced by recombinant and/or DNA shuffling; and salts, solvates, and other chemically modified forms of the sequence which retain the activity of the related sequence. Derivatives also include palindromes and reversals of the M2GlyR sequence, palindromes and reversals of portions of the M2GlyR sequence (such as some of the modules generated) and combinations of any of the above.

Sequences having or including a portion having at least about 35% sequence homology with any one of SEQ ID Nos. 4–47 are embraced within the present invention. Preferably, such sequences will have at least about 50% sequence homology with any one of SEQ ID Nos. 4–47, and still more preferably at least about 65% sequence homology with any one of SEQ ID Nos. 4–47.

Additionally, derivatives of the M2GlyR sequence which have their solubilities modified to a level of at least 5 mM and which exhibit similar properties to any one of SEQ ID Nos. 4, 9, 10, 13, 14, 18, 19, 21, 26–28, 32–35, that is sequences which exhibit greater than 15.0 $\mu A/cm^2$ at a peptide concentration of 500 $\mu M$ are embraced within the present invention. Preferably, these derivatives will have their solubilities modified by the addition of multiple polar amino acid residues on the C- or N-ends thereof. Moreover, it is preferred that these derivatives exhibit an activity profile of at least about 15.0 $\mu A/cm^2$ in MDCK cells at a level of 500 $\mu M$. More preferably, these derivatives will have an activity profile of at least about 15.0 $\mu A/cm^2$ in MDCK cells at a level of 300 $\mu M$, and still more preferably an activity profile of at least about 15.0 $\mu A/cm^2$ in MDCK cells at a level of 200 $\mu M$. Most preferably, such derivatives will have an activity profile of at least about 15.0 $\mu A/cm^2$ in MDCK cells at a level of 100 $\mu M$. Notably and advantageously, many of the generated sequences exhibited higher activity at lower concentrations than the previously known sequences (SEQ ID Nos. 1–3), thereby allowing a lower concentration of peptide to be used yet resulting in higher activity. It was also observed that, after certain peptide concentration levels had been reached, little or no increase in activity resulted. This tapering off of activity at higher concentrations should permit sequences having high activity at low concentrations to be used with a minimum amount of side effects due to excess peptide being used. Advantageously, this should also result in lower cost per dose, when used in treatment or therapy.

DETAILED DESCRIPTION OF THE PREFERRED EMBODIMENT

Figure 1:
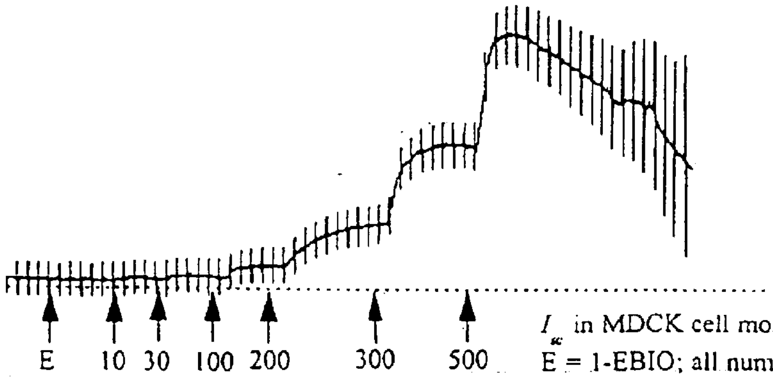
FIG. 1 is a graph illustrating the effect on $I_{sc}$ of a peptide in an MDCK cell monolayer wherein maximal effect occurs at a peptide concentration of at least 500 $\mu M$.

The following examples set forth preferred embodiments of the present invention. It is to be understood, however, that these examples are provided by way of illustration and nothing therein should be taken as a limitation upon the overall scope of the invention.

All summary results are presented as the arithmetic mean –SEM. The differences between control and treatment data were analyzed using ANOVA, Tukey (SAS Institute, Inc., Cary, N.C.), and Student's t-test (Excel, Microsoft Corporation, Redman, Wash.). The probability of making a type I error less than 0.05 was considered statistically significant.

EXAMPLE 1

This example generated the peptides and cell monolayers for subsequent testing. Additionally, epithelial electrical measurements were taken and activity profiles determined for a number of these generated peptides.

Materials and Methods

Peptide Synthesis.

The synthetic peptides based on the M2GlyR sequence were prepared using an automated solid-phase peptide synthetic technique. The peptides were prepared using the well documented, base-labile, Fmoc-strategy on an Applied Biosystems Model 431A peptide synthesizer (Perkin Elmer, Norwalk Conn.). All solvents were reagent grade unless otherwise indicated and the protected amino acids were purchased from one or more of the following vendors (Perkin Elmer, Norwalk Conn.; Bachem, Torrance Calif.; Peninsula Laboratories, Belmont Calif. and Peptides International, Louisville Ky.). A reaction scale of 0.1 mmol was employed. The resin, p-hydroxymethylphenoxymethyl polystyrene (HMP resin) was purchased with the first amino acid already attached and the degree of substitution calculated (0.51 mmol/g)(Perkin Elmer, Norwalk Conn.). The N-terminus of the resin bound amino acid was reversibly blocked with the $N^{\alpha}$–-fluorenylmethoxycarbonyl (Fmoc) protecting group and was weighed out and loaded into the reaction vessel (RV) of the synthesizer. The resin was first washed and swelled washed in the RV using 2×1.5 mL of N-Methylpyrrolidinone (NMP). The Fmoc group was subsequently removed by two sequential treatments with 4.5 mL of 22% piperidine (v/v) in NMP. The first deprotection was completed in 1 minute and the second after an additional 11 minutes. The resin was subsequently washed with 4×2.0 mL of NMP. The RV was drained and the resin was then ready to be coupled to the first incoming amino acid.

During the deprotection and washing steps outlined above, the incoming Fmoc-protected amino acid was preactivated to make it more reactive toward the resin-bound residue. The preactivation incubated 1-Hydroxybenzotriazole (HOBt) in the presence of the condensing agent 2-(1 H-benzotriazol-1-yl)-1,1,3,3-tetramethyluronium hexafluorophosphate (HBTU), thereby resulting in the formation of a highly reactive HOBt-amino acid ester. A ten-fold excess of amino acid (1.0 mmol) over resin sites was weighed out and transferred to a labeled plastic cartridge. Just prior to preactivation the amino acid was dissolved in 2.1 mL of NMP in the cartridge. This activation reaction begins upon the addition of 2.0–2.1 mL (0.9–0.95 mmol) of the 1:1; HOBt:HBTU in dimethylformamide (DMF) reagent. The amino acid was present in slight excess over the HOBt:HBTU in order to limit the possibility of undesirable side reactions. After the reaction had proceeded for 10 minutes at room temperature, 1.0 mL of 2M N,N-diisopropylethylamine (DIEA) was delivered to the amino acid cartridge, mixed briefly by bubbling argon and then the entire 5 mL solution was transferred to the RV. This transfer initiates the coupling of the incoming amino acid to the resin bound amino acid.

The coupling reaction proceeded for 25 minutes and was terminated by filtering off the soluble reactants. The resin was washed as described above and a second aliquot of preactivated HOBT ester-amino acid (prepared as described above) was added and allowed to react for 25 minutes. This second addition of the same amino acid was used to maximize the coupling efficiency of the amino acid to the resin. The first reaction usually results in about 95% efficiency and the second reaction increases it to about 99.5%. The remaining 0.5% sites were eliminated by a 5 minute reaction with 5 mL of a solution containing the following reactants in NMP at the given concentrations: 0.5 M acetic anhydride, 0.125 M DIEA, and 0.015 M HOBt. The RV was again drained and resin was subsequently washed with NMP as described above. The coupling of one amino acid to the resin was then complete. By maintaining high coupling efficiencies for the amino acids and then capping any low reactivity sites during the synthesis the number and diversity of failed or undesirable side products were significantly reduced, thus making the product easier to purify to homogeneity.

In order to add the next amino acid, the protocol outlined above was repeated with the appropriate N-Fmoc-protected amino acid. By the successive step-wise repetition of the deprotection, amino acid activation, and coupling steps, the entire sequence was assembled. The fully assembled resin bound peptide was finally washed with dichloromethane (DCM) and dried overnight under reduced pressure. The dried product was weighed and the overall synthetic yield was calculated based on a calculated theoretical 100% efficiency. For a 0.1 mmol scale synthesis, starting with 196 mg using a resin substitution of 0.510 mmol/g, the theoretical yield was 518 mg. Our average dried weight from 10 separate syntheses was 505 mg giving a calculated yield of 97.5% overall with a per step coupling efficiency of 99.88%.

The peptide was released from the resin and all side chain protecting groups were removed using a chemical cleavage reaction. In this reaction 500 mg of peptide/resin was incubated with 9.0 mL of trifluoroacetic acid (TFA) in the presence of 0.5 mL of 1,2-ethanedithiol and 0.5 mL of thioanisole at room temperature for 200 minutes. The mixture containing the cleaved peptide and by-products was removed from the solid resin support by filtration. The peptide was then precipitated by the addition of cold (4° C.) t-butyl methyl ether. The peptide precipitate was harvested by centrifugation and the ether containing the bulk of the cleavage by-products was decanted off. The precipitate was washed with the cold ether and recentrifuged a total of three times. The washed peptide was then dissolved in 20% acetic acid in water and extracted 3 more times with ether. After each extraction the ether layer was removed after a brief centrifugation. At this point the aqueous layer may be clear or slightly turbid. After these liquid-liquid extractions the water layer was shell frozen in a dry ice/ethanol bath and then dried by lyophilization. While the synthesis was complete at this point the peptide was not ready for administration to the cells.

The peptide produced above was purified to homogeneity by reversed-phase high performance liquid chromatography (RP-HPLC). The dried crude peptide (5 mg) was dissolved in 1.0 mL of TFE (Aldrich Chemical Co., Milwaukee Wis.). A 0.2 mL sample was injected onto a pre-equilibrated polystyrene based-$C_4$ semi-prep RP-HPLC column (PLRP-S 300 Å, 7.5×50 mm Polymer Laboratories, Amherst Mass.). The column was equilibrated 18% acetonitrile ($CH_3CN$) in deionized-distilled water containing 0.1% TFA at a flow rate of 2.0 mL/minute using a System Gold 125/166 computer controlled HPLC instrument (Beckman Instruments, Fullerton Calif.). After maintaining the 18% for three minutes post sample injection, a programmed gradient from 18% $CH_3CN$ to 54% $CH_3CN$ over 10 minutes was then executed. The column was maintained at 54% for 7 minutes and then jumped to 80% $CH_3CN$ followed by a 6 minute hold prior to returning to the initial conditions. The desired product eluted at 40.5% $CH_3CN$ and was observed by measuring the change in optical absorbance at 215 nm. Multiple runs using the HPLC were required to purify all of the peptide sample. The fractions containing the peptide from successive runs were pooled and lyophilized to dryness.

Sequence Confirmation:

To confirm the correct sequence has been assembled, an aliquot of the purified material is analyzed by both automated Edman sequencing and mass spectral analyses. For sequencing 25 picomoles are applied to a glass filter that has been pretreated with Biobrene® (Perkin Elmer, Norwalk Conn.) and allowed to dry. The filter is then sequenced using as Applied Biosystems Model 473A pulsed-liquid protein sequencer. All reagents used on this instrument are obtained from the instrument manufacturer. The sequence obtained by this method indicates that the correct amino acids have been added in the correct positions of the peptide. Mass spectral analysis is carried out using a Lasermat 2000 matrix assisted laser desorption ionization time of flight spectrometer (MALDITOF)(Finnigan Corp., San Jose Calif.). The peptide 1 pmol in 1 μL of 40% $CH_3CN$ in water is mixed with 1 μL of a 10 mg/mL solution of α-Cyano-4-hydroxycinnamic acid (Aldrich, Milwaukee Wis.) dissolved in 60% acetonitrile ($CH_3CN$) in deionized-distilled water containing 0.1% TFA along with 1 μL of a 20 μM solution of the standard peptide, substance P (Bachem Inc., Torrance Calif.), with a known mass of 1348.6 Da for the MH+1 ion. After the sample is mixed 1 μL is transferred to the etched center of a stainless steel sample slide and allowed to dry.

Once dry, the sample is placed in the instrument and the mass determined at the lowest power that yields signal using the added standard to calibrate the instrument. A single observed mass was obtained for each of the purified M2GlyR peptides and these values were in agreement with the predicted values calculated from the sum of the individual amino acid masses. Together these two analyses indicate that the correct sequences were assembled, there were no detectable modifications to the sequence and that no detectable contaminants were present in the purified peptide sample.

Cell culture:

MDCK cells were a generous gift of Dr. Lawrence Sullivan (Kansas University Medical Center, Kansas City, Kans.). T84 cells were obtained from Dr. Daniel Devor (University of Pittsburgh, Pittsburgh, Pa.). MDCK and T84 cells were maintained with similar culture procedures. The culture medium was a 1:1 mixture of DMEM and Ham's F-12 (Gibco BRL, Grand Island, N.Y.) supplemented with 5% heat inactivated fetal bovine serum (BioWhittaker, Walkersville, Md.), and 1% penicillin and streptomycin (Gibco BRL). Cells were grown in plastic culture flasks in a humidified environment with 5% $CO_2$ at 37° C. and passaged every 5–7 days. For Ussing chamber experiments, cells were plated on 1.13 $cm^2$ permeable supports (Snapwell, Costar, Cambridge, Mass.) at a density of approximately $1\times10^6$ cells/well and incubated in DMEM/F-12 supplemented with FBS and antibiotics (changed every other day) for 2–3 weeks prior to being mounted in modified Ussing flux chambers.

To form monolayers, the cells were plated onto the upper surface of a permanent membrane that forms the bottom of a plastic well. Two types were used. One was the Transwell-Col insert (CoStar Co., Cambridge, Mass.) supported in a six-well tissue culture plate and the other type was the Snapwell (CoStar Co., Cambridge, Mass.). During incubation, the medium was replaced at 48–72 hour intervals. Confluent monolayers formed within 72 hours. Experiments were performed on the monolayers 6–9 days after the initial plating. Net fluid secretion responses were optimal after six days.

Solutions:

Ringer's solution was made fresh daily. The final concentration (in mM) was 120 NaCl, 25 $NaHCO_3$ 3.3 $KH_2HPO_4$, 0.8 $K_2HPO_4$, 1.2 $MgCl_2$, 1.2 $CaCl_2$, (290±2 mOsmol). All components of the Ringer's solution were from Sigma (St. Louis, Mo.).

Electrophysiology Chemicals:

Stock solutions of chemicals were prepared as follows: forskolin (*Coleus forskohlii*, Calbiochem, La Jolla, Calif.), 10 mM in ethanol; 1-EBIO (Acros Organics), 1 M in dimethyl sulfoxide (DMSO); bumetanide (Sigma) 20 mM in ethanol; diphenylamine-2-dicarboxylic acid (DPC; Sigma), 1 M in DMSO; and 4,4'-Dinitrostilben-2,2'-disulfonic acid (DNDS; Acros Organics) 10 mM in Ringer's solution. The following stock solutions were prepared at 100 mM in DSMO; glibenclamide, indanyloxyacetic acid (R(+)-IAA-94), 2-[3-(trifluoromethyl)-anilino] nicotinic acid (niflumic acid; Sigma), 5-nitro-2-(3-phenylpropylamino) benzoic acid (NPPB; RBI, Natick, Mass.). All other chemicals were purchased from Sigma and were of reagent grade unless otherwise noted.

Epithelial electrical measurements:

Transepithelial ion transport was evaluated in a modified Ussing chamber (Model DCV9, Navicyte, San Diego, Calif.). The Ussing chamber's fluid resistance compensation was completed in Ringer's solution (see below). For electrical measurements cell monolayers were bathed in Ringer's solution maintained at 37° C. and continuously bubbled with 5% $CO_2$:95% $O_2$. The transepithelial membrane potential ($V_{te}$) was clamped to zero and the transepithelial short circuit ($I_{sc}$), an indicator of net ion transport, was measured continuously with a voltage clamp apparatus (Model 558C, University of Iowa, Department of Bioengineering, Iowa City, Iowa). Data were digitally acquired at 1 Hz with a Macintosh computer (Apple Computer, Cuppertino, Calif.) using Aqknowledge software (ver. 3.2.6, BIOPAC Systems, Santa Barbara, Calif.) with an MP100A-CE interface.

Results

Table 1 provides the results of this example. The peptide sequences generated are identified as SEQ ID Nos. 1–53. Measured activity for these sequences is provided as $\mu A/cm^2$ at specific peptide concentrations.

TABLE 1

Activity profile in MDCK cells for Palindromic M2GlyR sequence module and variants

| Seq. ID # | Amino Acid Sequence | Name | Activity μA/cm2 |
|---|---|---|---|
| 1 | PARVGLGITT VLTMTTQSSG SRA | M2GlyR | 1.5 at 500 μM |
| 2 | PARVGLGITT VLTMTTQSSG SRAKKKK | $CK_4$M2GlyR or $CK_4$ALB | 12.5 at 500 μM |
| 3 | KKKKPARVGL GITTVLTMTT QSSGSRA | $NK_4$M2GlyR or $NK_4$ALB | 15.9 at 500 μM |
| 4 | KKKKARSGSS QTTMTLVTTI GLGVRAA | $NK_4$bLa' | 18.7 at 300 μM |
| 5 | KKKKVTTIGL GVRAPLVTTI GLGVRAA | $NK_4$aLa' | <1.0 at 500 μM |
| 6 | KKKKTMTTQS SGSRALTMTT QSSGSRA | $NK_4$BLB | <1.0 at 500 μM |
| 7 | KKKKTMTTQS SGSRALVTTI GLGVRAA | $NK_4$BLa | <1.0 at 500 μM |
| 8 | KKKKVTTIGL GVRAPLARSG SSQTTMT | $NK_4$aLb | <1.0 at 500 μM |
| 9 | KKKKAARVGL GITTVWVTTI GLGVRAA | $NK_4$A'Wa' | 20.0 at 100 μM |
| 10 | KKKKPARVGL GITTVWTMTT QSSGSRA | $NK_4$AWB | 20.0 at 500 μM |
| 11 | KKKKPARVGL GITTVTTMIT QSSGSRA | $NK_4$ATB | NT |

TABLE 1-continued

Activity profile in MDCK cells for Palindromic M2GlyR sequence module and variants

| Seq. ID # | Amino Acid Sequence | Name | Activity μA/cm2 |
|---|---|---|---|
| 12 | KKKKPARVGL GITTVLTMTT QSSGSRAW | $NK_4$ALBW | NT |
| 13 | KKKKPARVGL GITTVLTMTT RS | $NK_4$ p22Q → R | 24.0 at 500 μM |
| 14 | KKKKPARVGL GITTVLTMTT QR | $NK_4$ p22S → R | 20.0 at 500 μM |
| 15 | KKKKPARVGL GITTVLTRTT QS | $NK_4$ p22M → R | <1.0 at 500 μM |
| 16 | KKKKARSGSS QTTMTLVTTI GLGVRAP | $NK_4$bLa | NT |
| 17 | ARSGSSQTTM TLVTTIGLGV RAPKKKK | $CK_4$bLa | 3.6 at 500 μM |
| 18 | KKKKPARVGL GITTVLVTTI GLGVRAP | $NK_4$ALa | 17.4 at 100 μM |
| 19 | PARVGLGITT VLVTTIGLGV RAPKKKK | $CK_4$ALa | 43.3 at 200 μM |
| 20 | KKKKPARVGL GITTVLPARV GLGITTV | $NK_4$ALA | <1.0 at 500 μM |
| 21 | KKKKPARVGL GITTVLAARV GLGITTV | $NK_4$ALA' | 8.0 at 250 μM |
| 22 | KKKKVTTIGL GVRAPLPARV GLGITTV | $NK_4$aLA | <1.0 at 500 μM |
| 23 | KKKKARSGSS QTTMTLTMTT QSSGSRA | $NK_4$bLB | 4.2 at 500 μM |
| 24 | KKKKTMTTQS SGSRALARSG SSQTTMT | $NK_4$BLb | <1.0 at 500 μM |
| 25 | KKKKARSGSS QTTMTLARSG SSQTTMT | $NK_4$bLb | <1.0 at 500 μM |
| 26 | KKKKPARVGL GITTVLVTTI GLGVRAA | $NK_4$ALa' | 25.7 at 100 μM |
| 27 | KKKKAARVGL GITTVLVTTI GLGVRAA | $NK_4$A'La' | 20.3 at 100 μM |
| 28 | KKKKAARVGL GITTVVTTIG LGVRAA | $NK_4$A'a' | 17.3 at 100 μM |
| 29 | KKKKAARVGL GITTVLLVTT IGLGVRAA | $NK_4$A'LLa' | NT |
| 30 | KKKKAARVGL GITTVLLLVT TIGLGVRAA | $NK_4$A'LLLa' | NT |
| 31 | KKKKAARVGL GITTVLLLLV TTIGLGVRAA | $NK_4$A'LLLLa' | NT |
| 32 | KKKKPARVGL GITTVLTRTT (DAP)S | $NK_4$-p22Q → DAP | 24.0 at 500 μM |
| 33 | KKKKPARVGL GITTVLTMTT QSSGS | $NK_4$ p25 | 18.4 at 500 μM |
| 34 | KKKKPARVGL GITTVLTMTT QS | $NK_4$ p22 | 20.3 at 500 μM |
| 35 | KKKKPARVGL GITTVLTMTT Q | $NK_4$ p21 | 13.1 at 500 μM |
| 36 | KKKKPARVGL GITTVLTMTT | $NK_4$ p20 | 8.8 at 500 μM |
| 37 | KKKKPARVGL GITTVLTMT | $NK_4$ p19 | 8.7 at 500 μM |
| 38 | KKKKPARVGL GITTVLTM | $NK_4$ p18 | 6.8 at 500 μM |
| 39 | KKKKPARVGL GITTVLT | $NK_4$ p17 | 1.8 at 500 μM |
| 40 | KKKKPARVGL GITTVL | $NK_4$ p16 | 1.5 at 500 μM |
| 41 | RVGLGITTVL TMTTQSSGSR AKKKK | $CK_4$ p25 | 6.3 at 500 μM |
| 42 | GLGITTVLTM TTQSSGSRAK KKK | $CK_4$ p22 | 3.3 at 500 μM |
| 43 | LGITTVLTMT TQSSGSRAKK KK | $CK_4$ p21 | <1.0 at 500 μM |
| 44 | GITTVLTMTT QSSGSRAKKK K | $CK_4$ p20 | <1.0 at 500 μM |
| 45 | ITTVLTMTTQ SSGSRAKKKK | $CK_4$ p19 | <1.0 at 500 μM |
| 46 | LTMTTQSSGS RAKKKK | $CK_4$ p16 | <1.0 at 500 μM |
| 47 | KKKKPARVGL GITTVLTMTT QSSGSRAKKK K | $NK_4$/$CK_4$ p31 | 5.0 at 500 μM |
| 48 | PARVGLGITT V | A | <1.0 at 500 μM |
| 49 | TMTTQSSGSR A | B | <1.0 at 500 μM |
| 50 | VTTIGLGVRA P | a | <1.0 at 500 μM |
| 51 | ARSGSSQTTM T | b | <1.0 at 500 μM |
| 52 | AARVGLGITT V | A' | <1.0 at 500 μM |
| 53 | VTTIGLGVRA A | a' | <1.0 at 500 μM |

Modules:
A = PARVGLGITTV
A' = AARVGLGITTV
a = VTTIGLGVRAP
a' = VTTIGLGVRAA
B = TMTTQSSGSRA
b = ARSGSSQTTMT As shown by these results, many derivatives of the M2GlyR sequence exhibited much greater activity at lower peptide concentrations than the M2GlyR sequence (SEQ ID No. 1) and the lysine-modified M2GlyR sequences (SEQ ID Nos. 2 and 3). For example, SEQ ID No. 26 exhibited nearly twice the activity at one-fifth of the concentration. In comparing SEQ ID No. 26 with SEQ ID No. 3, both sequences include four lysine residues at the N terminus, followed by the first eleven residues of the M2GlyR sequence, followed by a leucine residue. However, SEQ ID No. 3 further includes the remaining eleven residues of the M2GlyR sequence while SEQ ID No. 26 includes the first eleven residues of the M2GlyR sequence, in reverse order with an alanine substituted for the C-terminal proline residue. Thus, the modifications of the lysine-modified M2GlyR sequence resulting in the derivative M2GlyR sequence (SEQ ID No. 26) reduced the amount of peptide necessary to generate a high activity level in cell monolayers.

Additionally, FIGS. 1–5 illustrate the effects of M2GlyR derived sequences on $I_{sc}$ in MDCK monolayers. Each of these figures represents one testing run for each of the identified sequences. The numbers along the X axis represent the concentrations of peptide added at that point in the test. Total time along the X axis is 5 minutes. The Y axis represents a 5 $\mu$A response in the monolayer. As shown in these figures, the cell layer of FIG. 1 has little response until a 200 $\mu$A concentration of the peptide has been added to the monolayer, and significant results do not occur until a 500 $\mu$A concentration has been added. In contrast, the cell layer of FIG. 2 exhibits an almost immediate response to 100 $\mu$A peptide, and has maximal response to a peptide concentration of 200 $\mu$A. An even greater response is shown by the cell layers of FIGS. 3 and 4, which both had maximal response to peptide concentrations of 100 $\mu$A.

Figure 2:
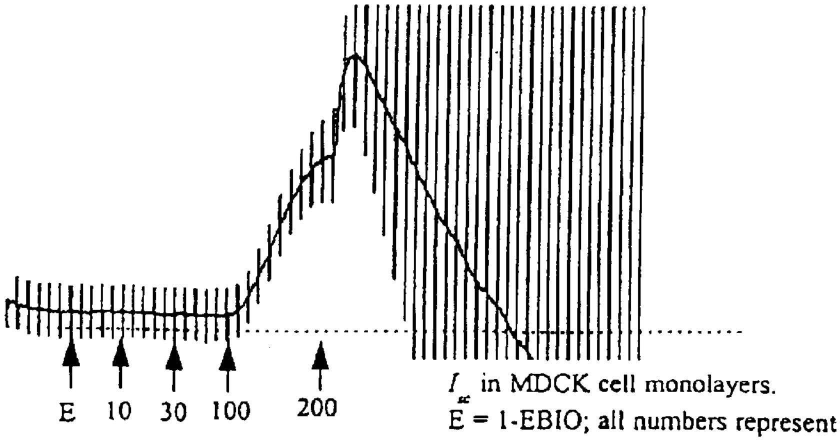
FIG. 2 is a graph illustrating the effect on $I_{sc}$ of a peptide in an MDCK cell monolayer wherein maximal effect occurs at a peptide concentration of at least 200 $\mu M$, and wherein the cell layer resistivity was greatly affected.
Figure 3:
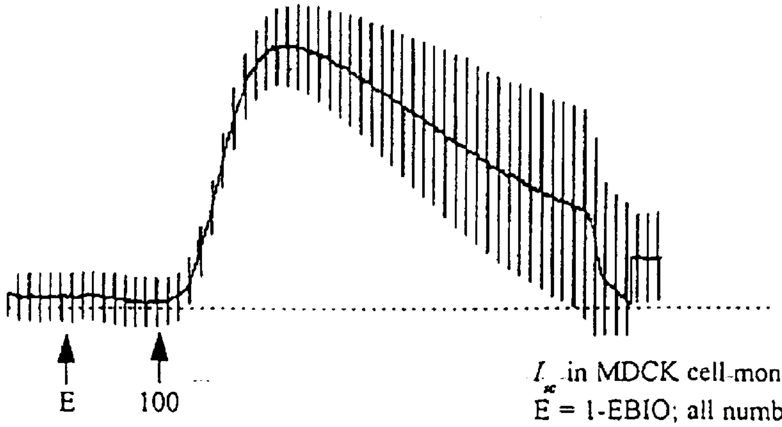
FIG. 3 is a graph illustrating the effect on $I_{sc}$ of a peptide in an MDCK cell monolayer wherein maximal effect occurs at a peptide concentration of at least 100 $\mu M$.
Figure 4:
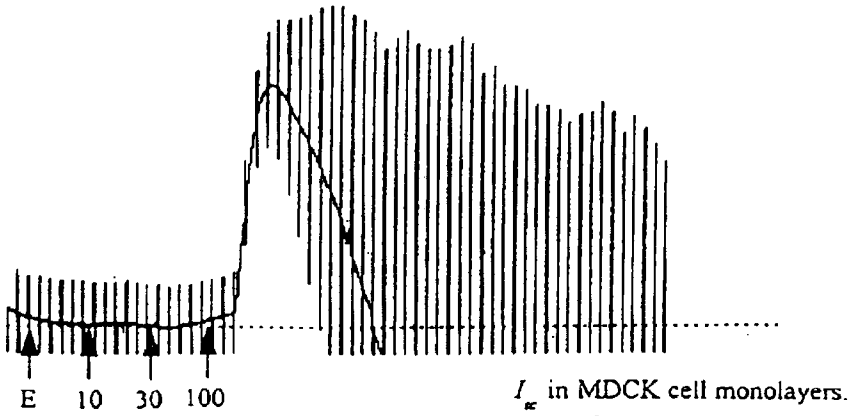
FIG. 4 is a graph illustrating the effect on $I_{sc}$ of a peptide in an MDCK cell monolayer wherein maximal effect occurs at a peptide concentration of at least 100 $\mu M$, and wherein the cell layer resistivity was greatly affected.
Figure 5:
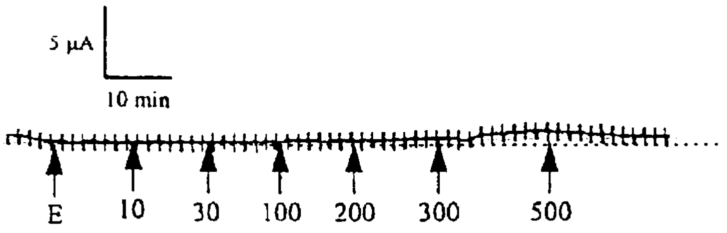
FIG. 5 is a graph illustrating the effect on $I_{sc}$ of a peptide in an MDCK cell monolayer wherein maximal effect occurs at a peptide concentration of at least 500 $\mu M$.

Another interesting result from these electrophysiology experiments was that the palindromic sequences generally had a negative effect on the resistivity of the cell monolayers. That is, continued exposure of the monolayers to the palindromic sequences resulted in a gradual breaking down of the monolayers, presumably through a breakdown of the cell-cell adhesions. This effect is not seen in isolated cells, and is present to varying extents with different sequences. FIGS. 1–5 illustrate this result by the height of the cross-hatch lines. For example, FIGS. 1 and 3 show moderate effects on the cell layer resistivity, as shown by their cross-hatch lines of moderate height. In contrast, FIG. 5 has cross-hatch lines of very low height, and little or no cell layer resistivity effects were noted. FIGS. 2 and 4 show cross-hatch lines of great height, and a large negative effect on the cell layer resistivity was noted. The appearance of activity in these figures is very rapid and once maximum activity was obtained, the cell resistivity became greatly affected. This resistivity effect could be reversed by the removal of the peptide from the monolayer or the experiment. Knowledge of these effects on resistivity will aid in the design of peptide therapies directed to particular cell layers. For example, peptides having a high negative effect on cell resistivity could be useful in treatment of cancer-type diseases by breaking down the cell layers of the cancerous-type mass. Such sequences could be useful in killing these undesirable cells.

EXAMPLE 2

This example generated computer models of peptides in order to observe orientation differences between different peptides.

Materials and Methods

All modeling studies were carried out on a Silicon Graphics Octane Workstation (Mountain View, Calif.) with IRIX64 release 6.5 as the operating system. Energy minimization and molecular dynamics were performed with SYBYL software (Tripos, Inc., St. Louis, Mo.). Peptides were built as alpha helices using the Biopolymer Module of SYBYL and subjected to 100 iterations of steepest descent minimization, followed by as many iterations as required to achieve convergence (gradient of <1 cal/mol A) using a conjugate gradient protocol. Kollman charges were used on the peptide molecules, as well as a dielectric of 4.0. Next, the psi, phi and omega angles were scanned to ensure they were within allowed conformational values and energy minimization using the Powell method was performed to minimize the energy of the models again. After the molecules were minimized, they were then subjected to simulated annealing protocol, in which they were heated to 500° K, allowed to equilibrated and the cooled to 300° K. Psi, $\phi$ and phi, $\Psi$ values were constrained between the amino and carboxyl arginines (the putative transmembrane portion of the molecule) in order to maintain the helical structure of the peptide. The lowest energy structures from this protocol were picked to form a long MD simulation of 250 ps at 300° K and the final structures were used to generate helical bundles.

Results

Figure 6A:
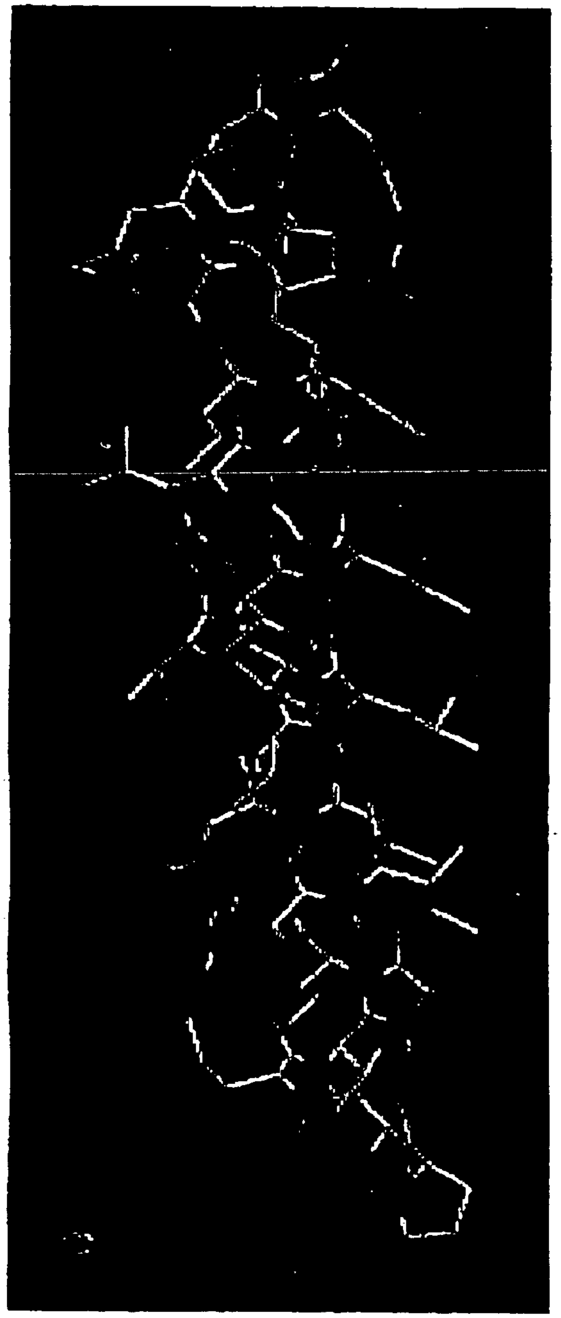
FIG. 6A is a computer model of C-$K_4$ A.L.a illustrating the folding of the C-terminal lysine residues.
Figure 6B:
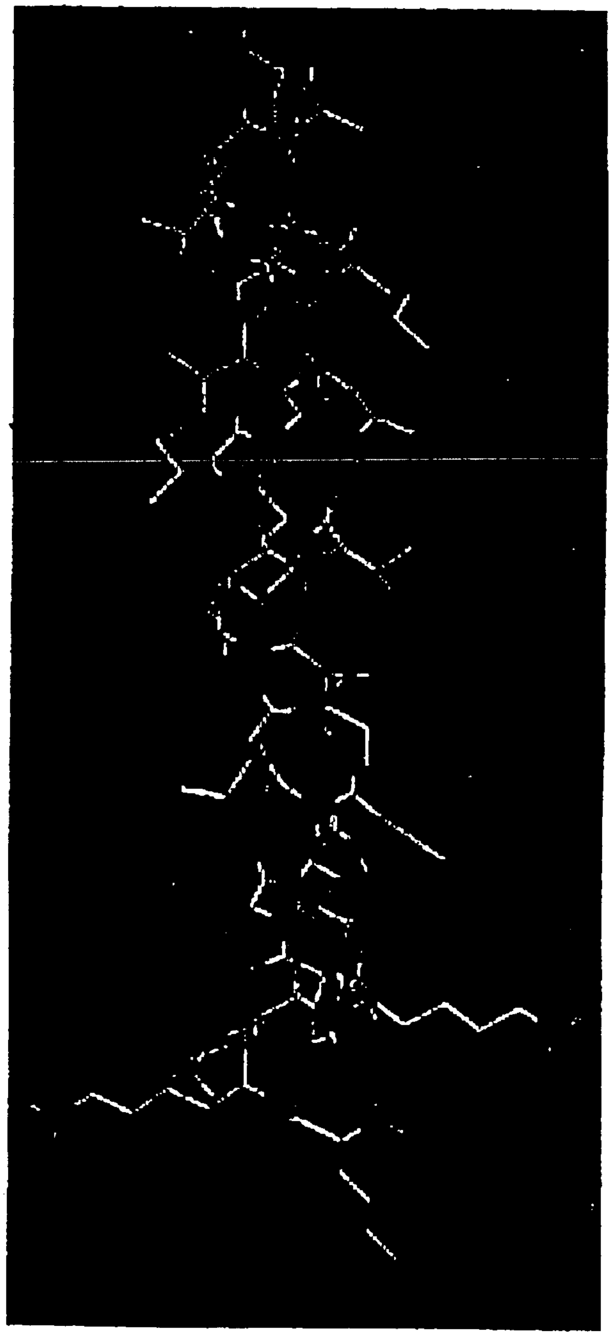
FIG. 6B is a computer model of N-$K_4$ A.L.a illustrating the extended confirmation of the N-terminal lysine residues.

Results of this example are given in FIGS. 6*a* and 6*b* which illustrate the computer models for $CK_4$A.L.a and $NK_4$A.L.a, respectively. Similar to the structure of C-$K_4$M2GlyR ($CK_4$A.L.B), the palindrome C-$K_4$ A.L.a (FIG. 6*a*) had the four lysine residues at the C-terminus folded back. In this folded back orientation, two of these lysine residues had bonded with the helix backbone through hydrogen bonding. Unexpectedly, the same orientation was not found for the palindromic sequence N-$K_4$ A.L.a (FIG. 6*b*) which had the four lysine residues extended away from the helix, and not hydrogen bonded to the helix backbone. To verify these results, a synthetic peptide modified with a single lysine at the C-terminus was capped and the structure was observed using NMR. The C-capped structures also showed a moderate compression in the second turn of the helix at the amino terminus, thereby verifying the results obtained using the computer modeling. The implications of this structure on function are significant for transmembrane sequences. In designing the water soluble N-$K_4$ and C-$K_4$ derivatives, it was assumed that the lysine residues would be solvent exposed and also serve to restrict the membrane insertion of the peptides to only one orientation with the lysines remaining outside the membrane. Having the lysines at either terminus should have allowed for the insertion of the peptide with its helix dipole oriented exclusively in one direction. Therefore any assemblage of the inserted sequences should be the result of bundles of parallel helices.

However based on the computer models, the predicted folding back of the lysines in the case of C-$K_4$ M2GlyR suggested that both orientations of the peptide were possible. Most models of the assembled pores formed by channel forming peptides have all helical dipoles parallel. In the case of C-$K_4$ M2GlyR having both orientations of the dipole possible within the membrane would interfere with the assembly of an active synthetic channel. Early modeling studies on M2 have suggested that anti-parallel packing of the helices leads to an assembly without a central pore. Thus, it is likely that an anti-parallel bundle of C-$K_4$ M2GlyR peptides would be non-functional. Before the possibility of multiple orientations within the membrane for C-$K_4$ was recognized, the working hypothesis was that the higher the concentration of monomer (in solution), gave rise to higher activity in cells. Now it appears that one must also consider (in the case of C-$K_4$ peptides) the concentration of peptide in the membrane with the correct orientation of dipoles as well as the competitive inhibition that might arise from complexation of helices with the opposite dipole.

EXAMPLE 3

This example utilized NMR to examine the aggregation tendencies of peptide sequences generated using the procedures of Example 1.

Materials and Methods

NMR was used to examine aggregation of the sequences as well as the conformational states of terminal lysine residues. TOCSY spectra were generated in water containing 10% D2O and 30% deuterated TFE for the different M2GlyR related sequences. Peptide concentrations of >3.0 mM were used to generate all spectra. Two-dimensional spectra were performed with a 11.75 T Varian Utility plus spectrometer operating at 499.96 MHz for 1H, with a 5 mm tripe-resonance inverse detection probe. NMR data sets were collected at 30° C. in water containing 30% deuterated TFE. A total of 256 increments of 2K data points were recorded with 100 ms mixing time. Before processing, the t1 dimensions of data sets of all experiments were zero-filled to 2K. 2D-1H-1H NOESY (Nuclear Overhauser Effect Spectroscopy) experiments were performed using a total of 256 increments of 4K data points which were recorded for these experiments. All data sets were collected in hypercomplex phase sensitive mode. These NOESY experiments were performed with 200, 300, 400 and 500 ms mixing times. Water peak suppression was obtained by low-power irradiation of the $H_2O$ peak during relaxation delay. TFE peak was considered as reference peak for chemical shift assignment. All data sets were collected in hypercomplex phase sensitive mode and were processed and analyzed using Varian NMR software VNMR 6.1B on a Silicon Graphics Indigo2 XZ workstation. When necessary, spectral resolution was enhanced by Lorenzian-Guassian apodization.

Results

Figure 7:
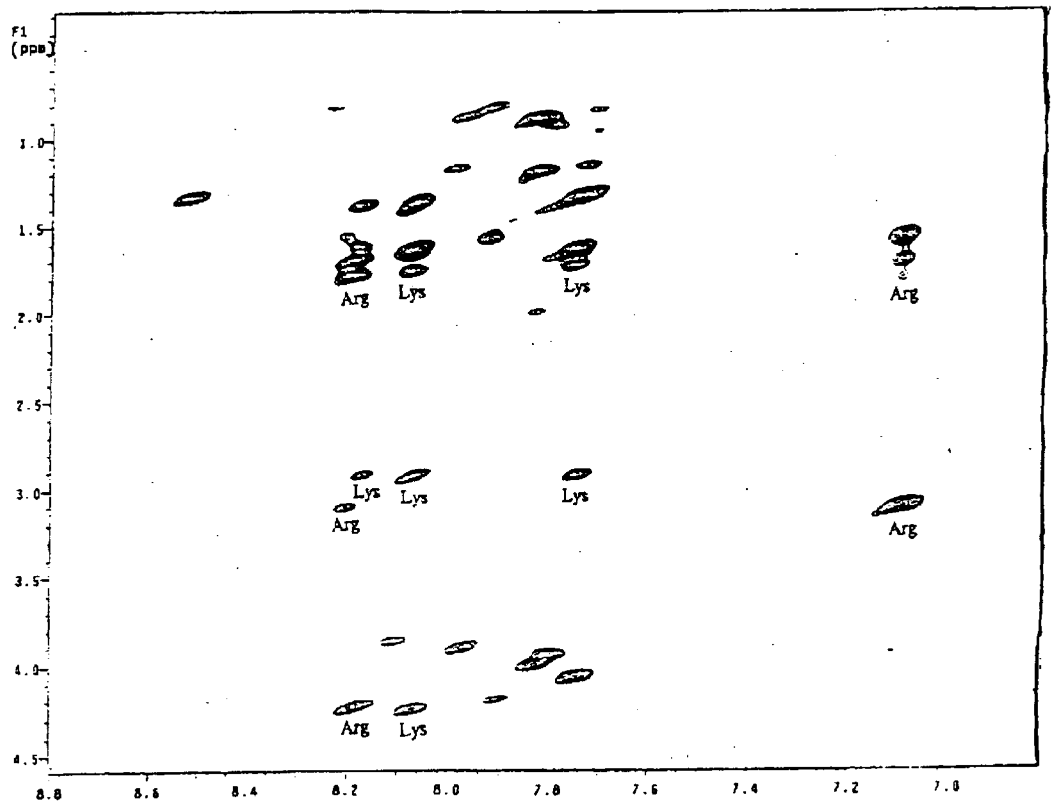
FIG. 7 is a TOCSY fingerprint region of C-$K_4$ A.L.a illustrating the upfield shifting of the lysine backbone amide protons and downfield shifting of side chain NH crosspeaks.
Figure 8:
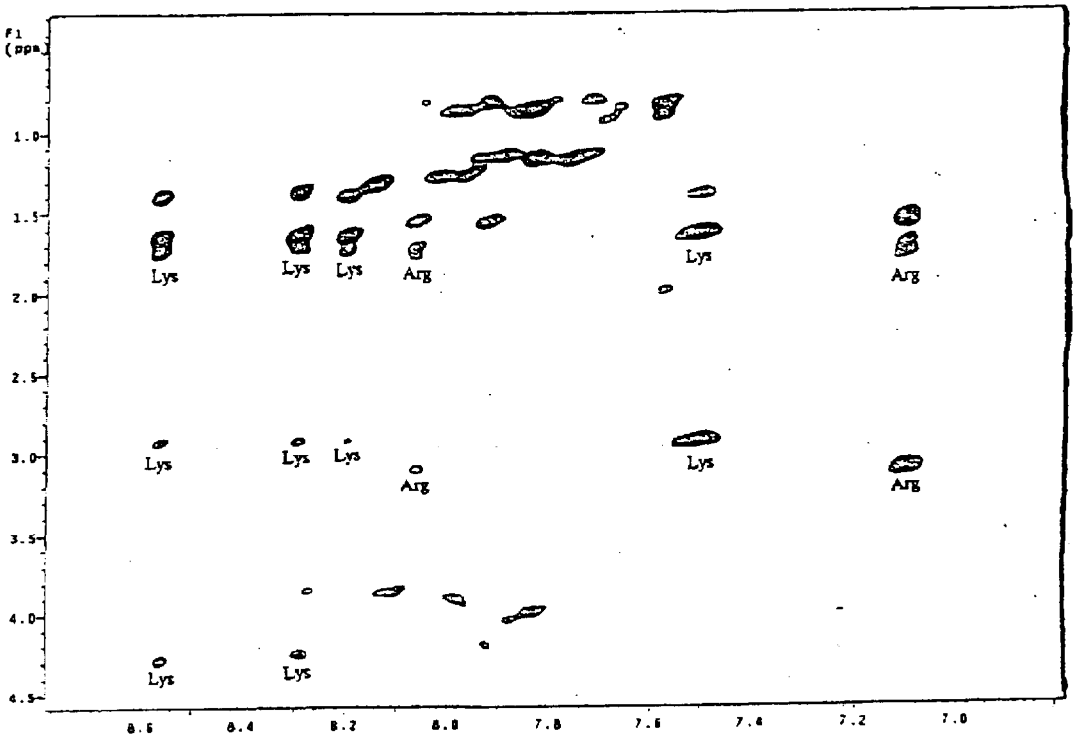
FIG. 8 is a TOCSY fingerprint region of N-$K_4$ A.L.a illustrating the downfield shifting of the lysine backbone amide protons and upfield shifting of side chain NH crosspeaks.

FIGS. 7 and 8 illustrate the TOCSY fingerprint regions of $CK_4$-A.L.a (SEQ ID No. 19) (FIG. 7) and $NK_4$-A.L.a (SEQ ID No. 18) (FIG. 8). Preliminary NMR data on N-$K_4$ A.L.a and $CK_4$-A.L.a shows the fingerprint region (NH to Ca and side chain proton connectivity) of 1H-1H 2D-TOCSY NMR spectra of these peptides recorded in water containing 30% deuterated TFE at 30° C. These spectra displayed reasonably sharp lines and the chemical shift dispersion. As shown in these Figures, the lysine backbone amide protons of $CK_4$-A.L.a have been shifted upfield and the side chain NH cross peaks have been shifted downfield, in comparison to $NK_4$-A.L.a. This confirms that the lysine backbone amide hydrogen is hydrogen-bonded and has folded side chains in $CK_4$-A.L.a and that the lysine residues for $NK_4$-A.L.a are extended and not hydrogen-bonded. Thus, these fingerprint regions verify the computer modeling results from Example 2.

EXAMPLE 4

This example determined the circular dichroism for various peptides generated using the methods of Example 1.

Materials and Methods

Circular dichroism:

Circular dichroism spectra were recorded on an Jasco Model J-720 spectropolarimeter in the range 180–250 nm using quartz cuvettes with a 0.2 mm pathlength. Eight scans recorded at a rate of 20 nm/minute were averaged and corrected for contributions of buffer (10 mM HEPES, pH 7.2). Peptide concentrations of 50 μM in 20% TFE were used to determine the helical propensity of the different M2GlyR analogs. The molar ellipticity was calculated using d-10-camphorsulfonic acid (290,5=7783° C. cm2 dmol 1) as a reference (Chen, G. C., and J. T. Yang. 1977. Two point calibration of spectropolarimeter with d-10-camphorsulfonic acid. *Anal. Lett.* 10:1195–1207.). The line shapes of the spectra were analyzed using a least-square fitting routine by comparison to polylysine standards representing 100% -helix, -turn, or random coil, respectively.

Results

Figure 9:
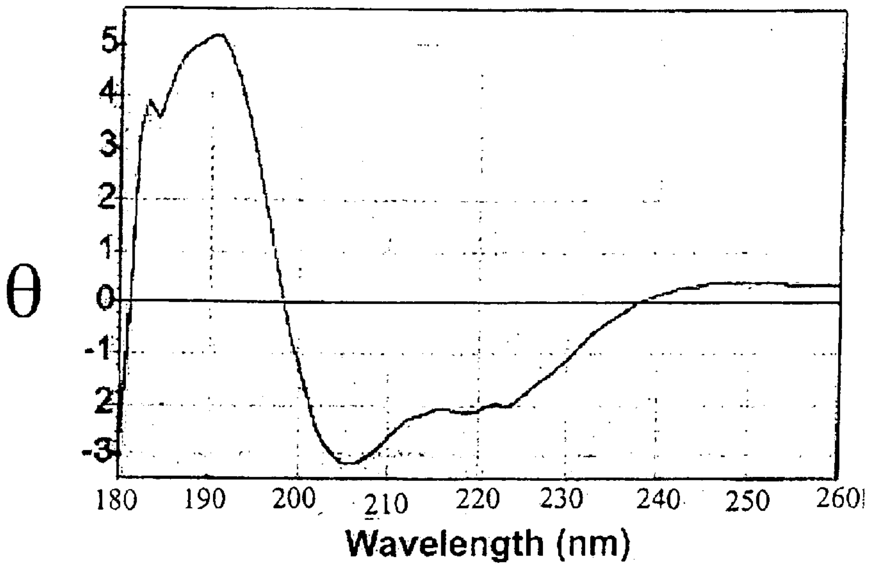
FIG. 9 is a circular dichroism spectra for a representative M2GlyR derivative depicting alpha helical content of an active peptide.
Figure 10:
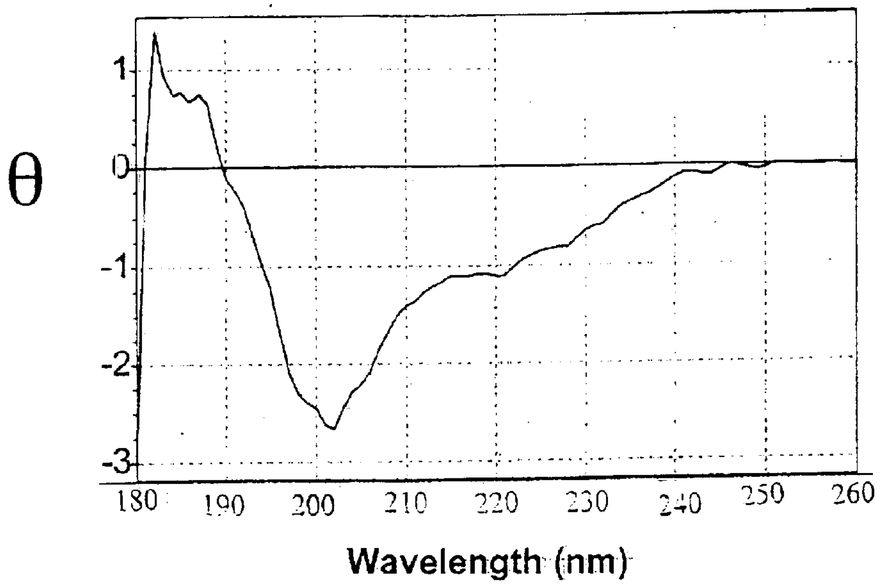
FIG. 10 is a circular dichroism spectra for a representative M2GlyR derivative depicting beta helical content of an inactive peptide.
Figure 11:
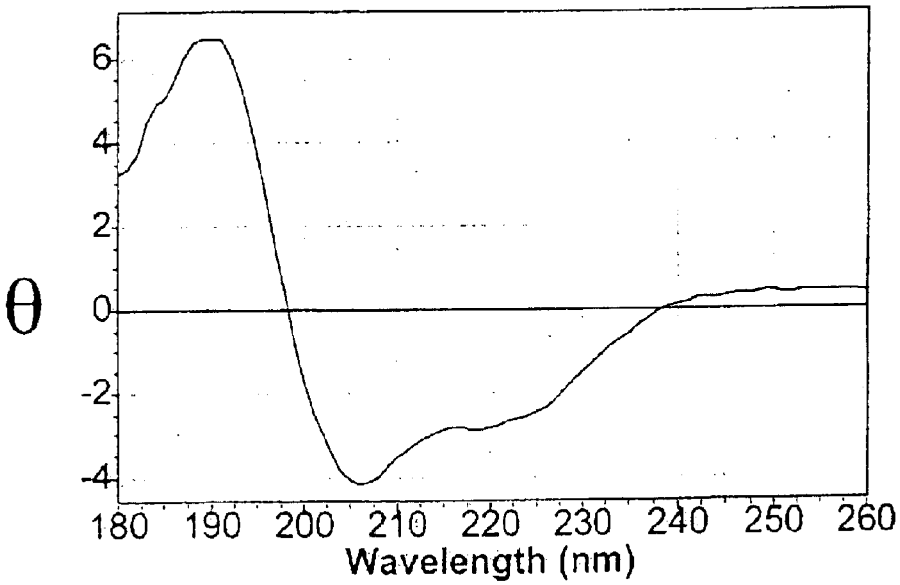
FIG. 11 is a circular dichroism spectra for a representative M2GlyR derivative depicting alpha helical content of an active peptide.

FIGS. 9–11 contain the circular dichroism spectra for three representative peptides. FIG. 9 shows the spectra for SEQ ID No. 26, FIG. 10 shows the spectra for SEQ ID No. 5, and FIG. 11 shows the spectra for SEQ ID No. 19. All spectra for these palindromes were determined in water containing 20% TFE. The spectra illustrated in FIGS. 9 and 11 are indicative of helical structure with minima at approximately 222 and 208 nm, respectively. Notably, each of these sequences are active in MDCK monolayers at 100 μM. These two sequences (SEQ ID Nos. 26 and 19) have their lysine caps on opposite ends but their helical content remains the same. In contrast, the spectra for SEQ ID No. 5 illustrated in FIG. 8 has its minima shifted, thereby indicating that the structure is not helical, but is rather beta-sheet. As shown in Table 1 and in FIG. 5, this sequence (SEQ D No. 5) has very little activity in MDCK monolayers. Thus, these results confirm that helical peptides, as determined by circular dichroism spectra, are much more active than non-helical sequences.

EXAMPLE 5

This example determined the emission fluorescence spectra for peptide sequences generated using the methods of Example 1. This example also tested tryptophan containing peptides for their ability to associate with and insert into bilayers.

Materials and Methods

Fluorescence:

Fluorescence was measured on a Hitachi Model F-4010 steady-state fluorescence spectrometer. All measurements were made in 10×10 mm quartz cuvettes at 37° C. Tryptophan fluorescence was excited at 280 nm with slits set to 5 nm. For samples containing vesicles, the background intensity was scaled appropriately and subtracted from the peptide-containing sample. Potassium iodide quenching measurements were performed by titrating a 4 M solution of KI, prepared daily, into a peptide solution and scanning the intensity of fluorescence from 300–400 nm stimulated by excitation at 280 nm. Stern-Volmer quenching constants $K_{S-V}$ were determined by linear regression with the equation $(F_0/F)$ $1+K_{S-V}[I]$, where F is the fluorescence intensity in the presence of iodide, $F_0$ is the fluorescence in the absence of iodide, and [I] is the molar concentration of iodide.

Liposome studies:

Liposomes are used to assess the propensity of different, tryptophan containing, channel-forming peptides to associate with and insert into bilayers. These events were followed using changes in the fluorescence intensity and emission maxima (blue shift) of the resident tryptophan residue. Lipids were obtained from Avanti Polar Lipids (Alabaster, Ala.) dissolved in chloroform and stored under nitrogen until used. A solution containing 1-palmitoyl-2-oleoyl-sn-glycero-3-phosphocholine(POPC; 22.5 wt %), 1-palmitoyl-2-oleoyl-sn-glycero-3 -phosphoserine (POPS; 10 wt %) and 1-palmitoyl-2-oleoyl-sn-glycero-3-phosphoethanolamine (POPE; 67.5 wt %) was prepared and the chloroform was evaporated with nitrogen. Lipids were then hydrated at a concentration of 11.1 mMol/L in a loading buffer containing (in mMol/L) 100 NaCl, 10 HEPES pH 7.4, for 60 minutes at 50° C. Large unilamaellar lipid vesicles were prepared by extrusion through a 2_m polycarbonate filter 17 times, then centrifuged at 37,500 rpm (125,000×g) in a TA865 rotor in a Sorvall ultracentrifuge (DuPont, Wilmington, Del.) for 60 minutes at 4° C. The supernatant was removed by aspiration and the pellet dissolved in external buffer.

For the peptide-liposome fluorescence studies are performed at 37° C. Buffer containing the liposomes were used to zero the instrument. Peptide is added to liposomes in heated cuvette and allowed to incubate for 10 minutes before scanning. Peptide concentrations were varied from a low of 5.0 μM up to a maximum of 300 μM. The lipid to protein Molar ratio varied from 2,200:1 at the lowest protein concentration up to 40:1 at the highest peptide concentration. Fluorescence quenching using potassium iodide (4.0 M stock) was also performed as described in the fluorescence section above.

Results

Figure 12:
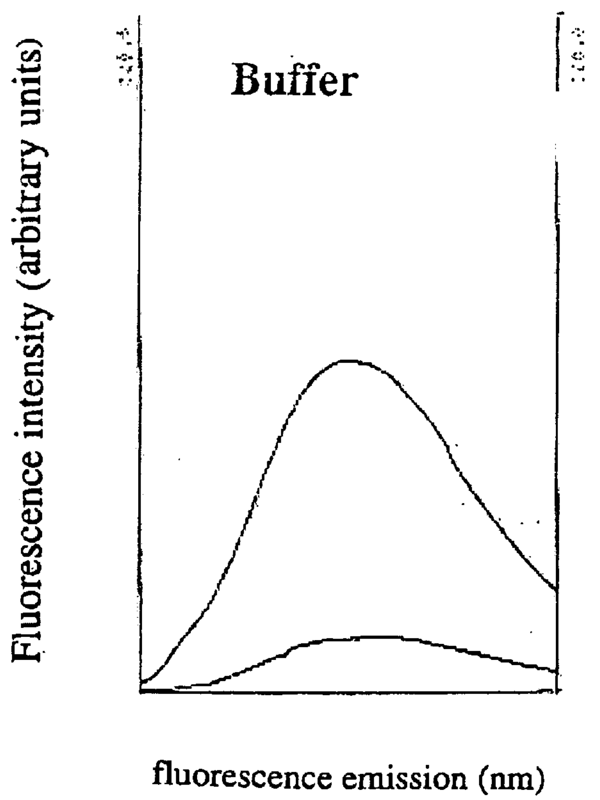
FIG. 12 is a graph of the fluorescence emission properties of a representative M2GlyR derivative in buffer illustrating the effect of a quencher agent.

FIG. 12 is the emission fluorescence spectra for SEQ ID No. 9 in aqueous buffer and in presence of 1 mM liposomes (90% POPC and 10% POPS). Buffer in both cases is 10 mM HEPES, 100 mM KCl at pH 7.4. Upper tracing in each panel has peptide (6.25 micromolar). Bottom tracing has final potassium iodide (KI) at a final concentration of 50 mM. KI is added to quench the fluorescence of the tryptophan residue.

As shown in FIG. 12, the tryptophan in buffer has a 348.4 nm lambda max. This value is consistent with the tryptophan (W) being filly exposed to solvent. The intensity is 148.0 (this is in arbitrary units). The near complete quenching (illustrated by the lower line) with 50 mM KI confirms the full exposure of W to solvent. Thus, once the KI was added, the lambda max changed to 357.0 nm and the intensity dropped to 26.7.

Figure 13:
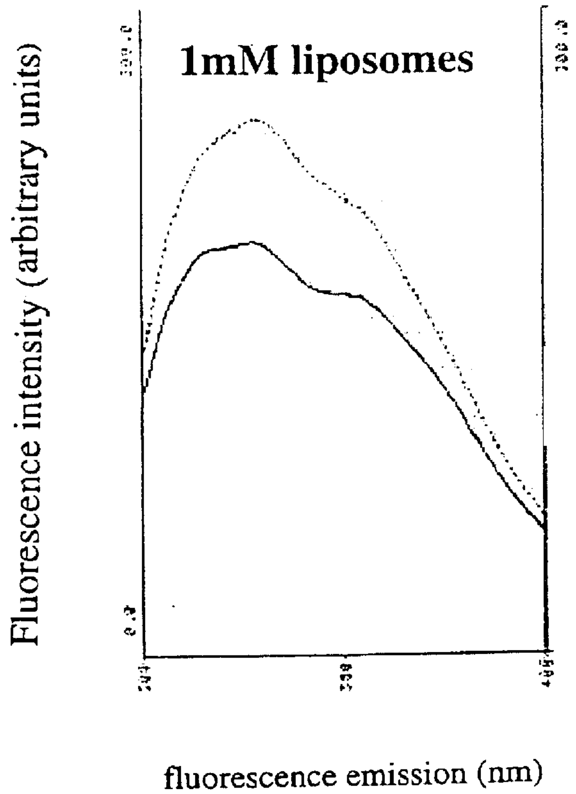
FIG. 13 is a graph of the fluorescence emission properties of a representative M2GlyR derivative in liposomes illustrating the effect of a quencher agent.

When the peptide is added to liposomes, the lambda max decreases slightly, however, the intensity is greatly increased. Additionally, the addition of the quenching agent does not have as great of an effect on the peptide in the buffer solution. As shown in FIG. 13, there is both a blue shift of the lambda max to 327.8 nm (so-called blue shift) with a doubling of the fluorescence intensity to approximately 249.0. This large shift in the presence of lipid indicates that the W residue is buried in the membrane. When the quenching agent (KI) is added, the intensity decreases to 193.0 and the lambda max drops only 0.4 nm to 327.4 nm. The weak quenching with KI indicates a shielding from solvent which is not membrane permeable, thereby confirming the membrane association of the W. The very large blue shift also suggests a deep burying which suggests that the peptide is in a transmembrane or membrane spanning configuration as opposed to a simple membrane association without insertion. Additionally, the binding of the peptide to the membrane is almost instantaneous, as shown by the rapid onset of fluorescence.

EXAMPLE 6

This example determined the amount of aggregation exhibited by peptides generated using the methods of Example 1.

Materials and Methods

Chemical cross-linking:

In order to visualize the oligomeric state of the peptide in solution a chemical cross-linking protocol was developed. Calculated amounts of each peptide were weighted out and dissolved in 1 mL of distilled water to make 1 mM stock solutions. A 100 mM stock solution of the chemical crosslinking reagent Bis [Sulfosuccinimidyl] suberate, $BS^3$, (Pierce Chemical Co., Rockford, Ill.) was prepared in dimethyl sulfoxide (DMSO). In typical reactions, 5–30 μL of 1.0 mM stock solution of peptide are added to 64–94 μL of 10 mM HEPES buffer, pH 8.1 to give a range of concentrations starting at 50 μM rising up to 300 μM. Sample were allowed to sit at room temperature for 15 minutes. 1–6 μL of 100 mM $BS^3$ was then added to the previously prepared peptide such that the crosslinking reagent was present in 20-fold excess. The final volume for each reaction was 100 μL. After reacting for 30 minutes, the reaction was stopped with the addition of 10 μL 1.0 N HCl. Each sample was then vacuum dried. Later dry samples were re-dissolved in 60 μL of distilled water along with 60 μL of a 2×-tricine SDS sample buffer (Novex, San Diego). All samples were then boiled at 100° C. for 5 minutes. 5 μL aliquots of each SDS boiled sample was then loaded into separate lanes of pre-cast, 1.0 mm, 10 well, 10–20% tricine gels (Novex, San Diego). Pre-made Novex tricine-SDS buffer was used in the electrophoresis. The reference well contained 1 μL of Multi-Mark® multi-colored molecular weight standard (Novex, San Diego). The electrophoresis was carried out at a constant 110 Volts for 90 minutes. The gel was then fixed in 40% methanol in water and the cross-linked peptides visualized using silver staining (SilverXpress® silver staining kit, Invitrogen, Carlsbad, Calif.).

Results

Figure 14:
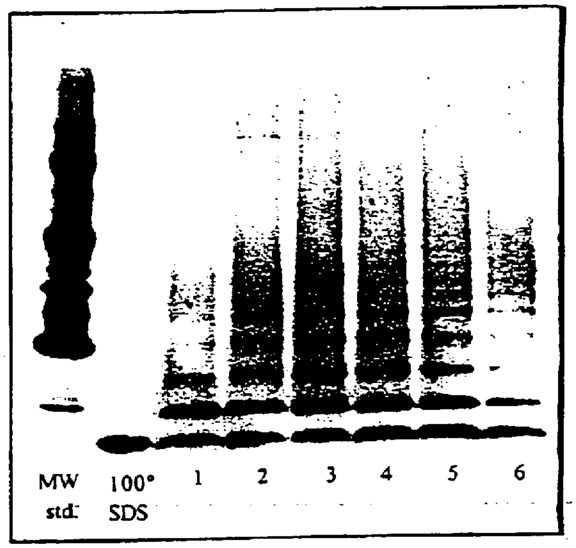
FIG. 14 is a photograph of an SDS-PAGE gel illustrating the multimeric species of representative M2GlyR derivatives.
Figure 14:
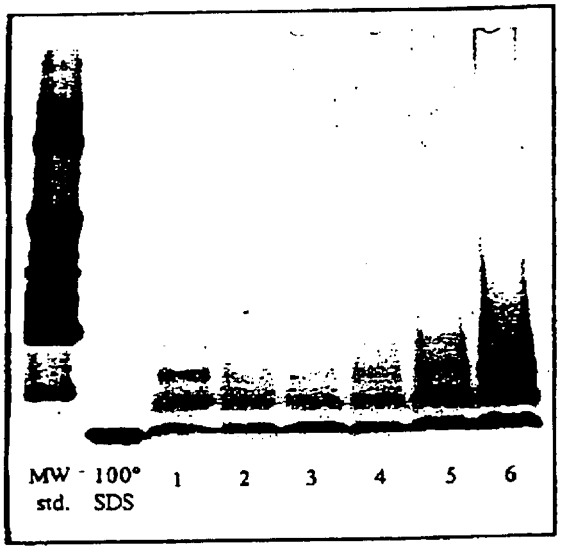
Figure 15:
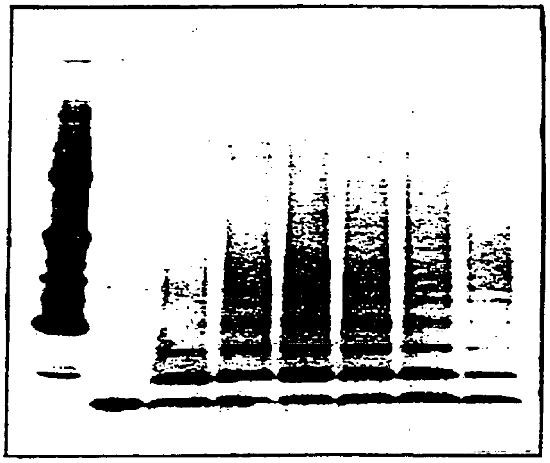
FIG. 15 is a photograph of an SDS-PAGE gel illustrating the multimeric species of representative M2GlyR derivatives.
Figure 15:
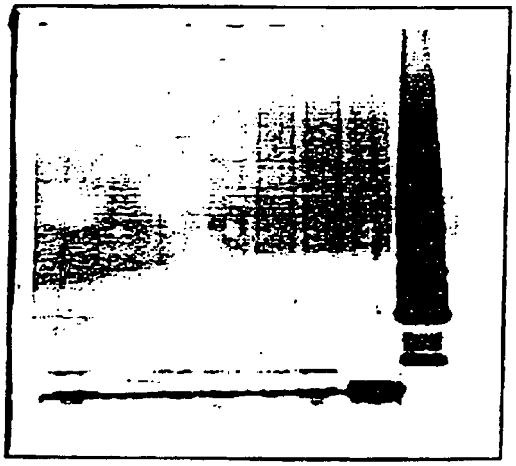

Representative results for this Example are provided in FIGS. 14 and 15 which illustrate the aggregate numbers for SEQ ID Nos. 2,3 and 18. Physical data from other experiments support the modeling data described above. As shown by FIG. 14, N-$K_4$ M2GlyR (SEQ ID No. 3) gave a ladder of bands starting from monomer up to assemblies approaching 36 kDa. However, C-$K_4$ M2GlyR (SEQ ID No. 2) showed only trace amounts of aggregates higher than trimer. Assuming that the lysines are participating in hydrogen bonds with the backbone carbonyls, two postulates can be proposed; 1) the lysine ε-amino groups are not readily available for cross-linking, or 2) the lysine C-capping disrupts the ability to form the pores in membranes or form aggregates in solution. FIG. 15 compares the results for SEQ ID No. 3 with a palindrome of that sequence, SEQ ID No. 18. SEQ ID No. 18 is related to SEQ ID No. 3 in that the first 12 residues (the first 11 residues comprise module A and the 12th is leucine)are identical and the remaining 11 amino acid residues are the A module in reverse. The result is a decrease in multimers as SEQ ID No. 3 comprised 12 or more aggregates while SEQ ID No. 18 was >90% monomeric with only a trace of dimer. As the number of aggregates decreased, the activity increased greatly (see Table 1).

Figure 16:
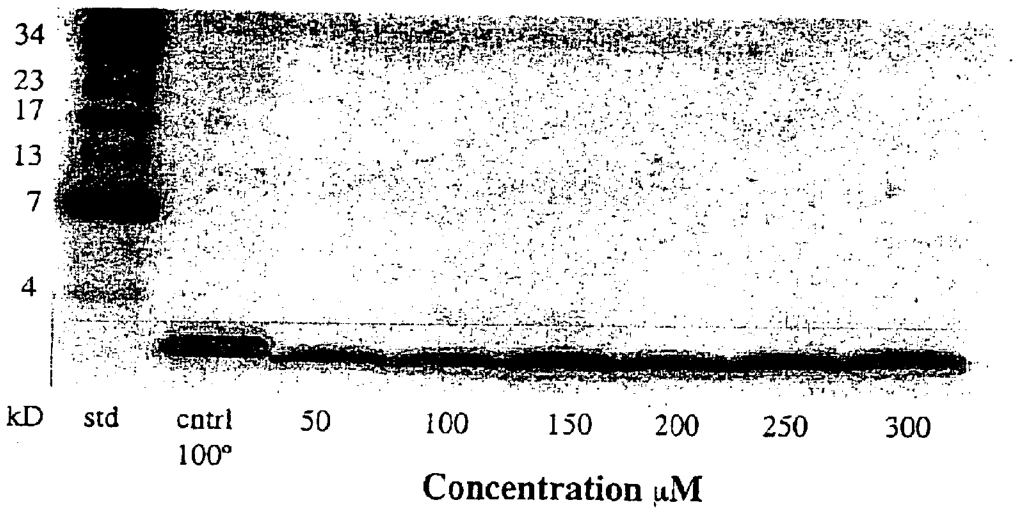
FIG. 16 is a photograph of a gel illustrating the concentration dependence of cross-linking of a representative M2GlyR derivative.

Another representative figure for this Example is FIG. 16 which illustrates the concentration dependence of cross-linking for SEQ ID No. 9. As shown in this Figure, increasing concentrations of the peptide did not result in peptide aggregation and the peptide remained in monomer form. As monomeric forms tend to have higher levels of activity, the stability of SEQ ID No. 9 at high concentrations would indicate relatively high activity. This was, in fact, the case for SEQ ID No. 9 which has an activity of 20.0 μA/$cm^2$ at a concentration of 100 μM.

We claim:

1. A method of altering the flux of water across an epithelial cell presenting first and second spaced apart surfaces, said method comprising the steps of:

a. providing a peptide capable of forming a channel assembly for transport of anions through said epithelial cell, said peptide having the sequence of SEQ ID NO. 18; and b. contacting said peptide with said first surface of said epithelial cell, and causing said peptide to alter the flux of water across said cell surface.

* * * * *

SEQUENCE LISTING

<160> NUMBER OF SEQ ID NOS: 53

<210> SEQ ID NO 1
<211> LENGTH: 23
<212> TYPE: PRT
<213> ORGANISM: Homo sapiens

<400> SEQUENCE: 1

```
Pro Ala Arg Val Gly Leu Gly Ile Thr Thr Val Leu Thr Met Thr Thr
1               5                   10                  15

Gln Ser Ser Gly Ser Arg Ala
            20
```

<210> SEQ ID NO 2
<211> LENGTH: 27
<212> TYPE: PRT
<213> ORGANISM: Modified Homo sapiens

<400> SEQUENCE: 2

```
Pro Ala Arg Val Gly Leu Gly Ile Thr Thr Val Leu Thr Met Thr Thr
1               5                   10                  15

Gln Ser Ser Gly Ser Arg Ala Lys Lys Lys Lys
            20                  25
```

<210> SEQ ID NO 3
<211> LENGTH: 27
<212> TYPE: PRT
<213> ORGANISM: Modified Homo sapiens

<400> SEQUENCE: 3

```
Lys Lys Lys Lys Pro Ala Arg Val Gly Leu Gly Ile Thr Thr Val Leu
1               5                   10                  15

Thr Met Thr Thr Gln Ser Ser Gly Ser Arg Ala
            20                  25
```

<210> SEQ ID NO 4
<211> LENGTH: 27
<212> TYPE: PRT
<213> ORGANISM: Modified Homo sapiens

<400> SEQUENCE: 4

```
Lys Lys Lys Lys Ala Arg Ser Gly Ser Ser Gln Thr Thr Met Thr Leu
1               5                   10                  15

Val Thr Thr Ile Gly Leu Gly Val Arg Ala Ala
            20                  25
```

<210> SEQ ID NO 5
<211> LENGTH: 27
<212> TYPE: PRT
<213> ORGANISM: Modified Homo sapiens

<400> SEQUENCE: 5

```
Lys Lys Lys Lys Val Thr Thr Ile Gly Leu Gly Val Arg Ala Pro Leu
1               5                   10                  15

Val Thr Thr Ile Gly Leu Gly Val Arg Ala Ala
            20                  25
```

<210> SEQ ID NO 6
<211> LENGTH: 27
<212> TYPE: PRT
<213> ORGANISM: Modified Homo sapiens -continued

<400> SEQUENCE: 6

```
Lys Lys Lys Lys Thr Met Thr Thr Gln Ser Ser Gly Ser Arg Ala Leu
1               5                   10                  15

Thr Met Thr Thr Gln Ser Ser Gly Ser Arg Ala
            20                  25
```

<210> SEQ ID NO 7
<211> LENGTH: 27
<212> TYPE: PRT
<213> ORGANISM: Modified Homo sapiens

<400> SEQUENCE: 7

```
Lys Lys Lys Lys Thr Met Thr Thr Gln Ser Ser Gly Ser Arg Ala Leu
1               5                   10                  15

Val Thr Thr Ile Gly Leu Gly Val Arg Ala Ala
            20                  25
```

<210> SEQ ID NO 8
<211> LENGTH: 27
<212> TYPE: PRT
<213> ORGANISM: Modified Homo sapiens

<400> SEQUENCE: 8

```
Lys Lys Lys Lys Val Thr Thr Ile Gly Leu Gly Val Arg Ala Pro Leu
1               5                   10                  15

Ala Arg Ser Gly Ser Ser Gln Thr Thr Met Thr
            20                  25
```

<210> SEQ ID NO 9
<211> LENGTH: 27
<212> TYPE: PRT
<213> ORGANISM: Modified Homo sapiens

<400> SEQUENCE: 9

```
Lys Lys Lys Lys Ala Ala Arg Val Gly Leu Gly Ile Thr Thr Val Trp
1               5                   10                  15

Val Thr Thr Ile Gly Leu Gly Val Arg Ala Ala
            20                  25
```

<210> SEQ ID NO 10
<211> LENGTH: 27
<212> TYPE: PRT
<213> ORGANISM: Modified Homo sapiens

<400> SEQUENCE: 10

```
Lys Lys Lys Lys Pro Ala Arg Val Gly Leu Gly Ile Thr Thr Val Trp
1               5                   10                  15

Thr Met Thr Thr Gln Ser Ser Gly Ser Arg Ala
            20                  25
```

<210> SEQ ID NO 11
<211> LENGTH: 27
<212> TYPE: PRT
<213> ORGANISM: Modified Homo sapiens

<400> SEQUENCE: 11

```
Lys Lys Lys Lys Pro Ala Arg Val Gly Leu Gly Ile Thr Thr Val Thr
1               5                   10                  15

Thr Met Thr Thr Gln Ser Ser Gly Ser Arg Ala
            20                  25
```

-continued

<210> SEQ ID NO 12
<211> LENGTH: 28
<212> TYPE: PRT
<213> ORGANISM: Modified Homo sapiens

<400> SEQUENCE: 12

```
Lys Lys Lys Lys Pro Ala Arg Val Gly Leu Gly Ile Thr Thr Val Leu
1               5                   10                  15

Thr Met Thr Thr Gln Ser Ser Gly Ser Arg Ala Trp
            20                  25
```

<210> SEQ ID NO 13
<211> LENGTH: 22
<212> TYPE: PRT
<213> ORGANISM: Modified Homo sapiens

<400> SEQUENCE: 13

```
Lys Lys Lys Lys Pro Ala Arg Val Gly Leu Gly Ile Thr Thr Val Leu
1               5                   10                  15

Thr Met Thr Thr Arg Ser
            20
```

<210> SEQ ID NO 14
<211> LENGTH: 22
<212> TYPE: PRT
<213> ORGANISM: Modified Homo sapiens

<400> SEQUENCE: 14

```
Lys Lys Lys Lys Pro Ala Arg Val Gly Leu Gly Ile Thr Thr Val Leu
1               5                   10                  15

Thr Met Thr Thr Gln Arg
            20
```

<210> SEQ ID NO 15
<211> LENGTH: 22
<212> TYPE: PRT
<213> ORGANISM: Modified Homo sapiens

<400> SEQUENCE: 15

```
Lys Lys Lys Lys Pro Ala Arg Val Gly Leu Gly Ile Thr Thr Val Leu
1               5                   10                  15

Thr Arg Thr Thr Gln Ser
            20
```

<210> SEQ ID NO 16
<211> LENGTH: 27
<212> TYPE: PRT
<213> ORGANISM: Modified Homo sapiens

<400> SEQUENCE: 16

```
Lys Lys Lys Lys Ala Arg Ser Gly Ser Ser Gln Thr Thr Met Thr Leu
1               5                   10                  15

Val Thr Thr Ile Gly Leu Gly Val Arg Ala Pro
            20                  25
```

<210> SEQ ID NO 17
<211> LENGTH: 27
<212> TYPE: PRT
<213> ORGANISM: Modified Homo sapiens

<400> SEQUENCE: 17

```
Ala Arg Ser Gly Ser Ser Gln Thr Thr Met Thr Leu Val Thr Thr Ile
```

-continued

```
1               5                   10                  15

Gly Leu Gly Val Arg Ala Pro Lys Lys Lys Lys
            20                  25


<210> SEQ ID NO 18
<211> LENGTH: 27
<212> TYPE: PRT
<213> ORGANISM: Modified Homo sapiens

<400> SEQUENCE: 18

Lys Lys Lys Lys Pro Ala Arg Val Gly Leu Gly Ile Thr Thr Val Leu
1               5                   10                  15

Val Thr Thr Ile Gly Leu Gly Val Arg Ala Pro
            20                  25


<210> SEQ ID NO 19
<211> LENGTH: 27
<212> TYPE: PRT
<213> ORGANISM: Modified Homo sapiens

<400> SEQUENCE: 19

Pro Ala Arg Val Gly Leu Gly Ile Thr Thr Val Leu Val Thr Thr Ile
1               5                   10                  15

Gly Leu Gly Val Arg Ala Pro Lys Lys Lys Lys
            20                  25


<210> SEQ ID NO 20
<211> LENGTH: 27
<212> TYPE: PRT
<213> ORGANISM: Modified Homo sapiens

<400> SEQUENCE: 20

Lys Lys Lys Lys Pro Ala Arg Val Gly Leu Gly Ile Thr Thr Val Leu
1               5                   10                  15

Pro Ala Arg Val Gly Leu Gly Ile Thr Thr Val
            20                  25


<210> SEQ ID NO 21
<211> LENGTH: 27
<212> TYPE: PRT
<213> ORGANISM: Modified Homo sapiens

<400> SEQUENCE: 21

Lys Lys Lys Lys Pro Ala Arg Val Gly Leu Gly Ile Thr Thr Val Leu
1               5                   10                  15

Ala Ala Arg Val Gly Leu Gly Ile Thr Thr Val
            20                  25


<210> SEQ ID NO 22
<211> LENGTH: 27
<212> TYPE: PRT
<213> ORGANISM: Modified Homo sapiens

<400> SEQUENCE: 22

Lys Lys Lys Lys Val Thr Thr Ile Gly Leu Gly Val Arg Ala Pro Leu
1               5                   10                  15

Pro Ala Arg Val Gly Leu Gly Ile Thr Thr Val
            20                  25


<210> SEQ ID NO 23
<211> LENGTH: 27
<212> TYPE: PRT
```

-continued

<213> ORGANISM: Modified Homo sapiens

<400> SEQUENCE: 23

Lys Lys Lys Lys Ala Arg Ser Gly Ser Ser Gln Thr Thr Met Thr Leu
1 5 10 15

Thr Met Thr Thr Gln Ser Ser Gly Ser Arg Ala
20 25

<210> SEQ ID NO 24
<211> LENGTH: 27
<212> TYPE: PRT
<213> ORGANISM: Modified Homo sapiens

<400> SEQUENCE: 24

Lys Lys Lys Lys Thr Met Thr Thr Gln Ser Ser Gly Ser Arg Ala Leu
1 5 10 15

Ala Arg Ser Gly Ser Ser Gln Thr Thr Met Thr
20 25

<210> SEQ ID NO 25
<211> LENGTH: 27
<212> TYPE: PRT
<213> ORGANISM: Modified Homo sapiens

<400> SEQUENCE: 25

Lys Lys Lys Lys Ala Arg Ser Gly Ser Ser Gln Thr Thr Met Thr Leu
1 5 10 15

Ala Arg Ser Gly Ser Ser Gln Thr Thr Met Thr
20 25

<210> SEQ ID NO 26
<211> LENGTH: 27
<212> TYPE: PRT
<213> ORGANISM: Modified Homo sapiens

<400> SEQUENCE: 26

Lys Lys Lys Lys Pro Ala Arg Val Gly Leu Gly Ile Thr Thr Val Leu
1 5 10 15

Val Thr Thr Ile Gly Leu Gly Val Arg Ala Ala
20 25

<210> SEQ ID NO 27
<211> LENGTH: 27
<212> TYPE: PRT
<213> ORGANISM: Modified Homo sapiens

<400> SEQUENCE: 27

Lys Lys Lys Lys Ala Ala Arg Val Gly Leu Gly Ile Thr Thr Val Leu
1 5 10 15

Val Thr Thr Ile Gly Leu Gly Val Arg Ala Ala
20 25

<210> SEQ ID NO 28
<211> LENGTH: 26
<212> TYPE: PRT
<213> ORGANISM: Modified Homo sapiens

<400> SEQUENCE: 28

Lys Lys Lys Lys Ala Ala Arg Val Gly Leu Gly Ile Thr Thr Val Val
1 5 10 15

Thr Thr Ile Gly Leu Gly Val Arg Ala Ala
20 25

-continued

<210> SEQ ID NO 29
<211> LENGTH: 28
<212> TYPE: PRT
<213> ORGANISM: Modified Homo sapiens

<400> SEQUENCE: 29

```
Lys Lys Lys Lys Ala Ala Arg Val Gly Leu Gly Ile Thr Thr Val Leu
1               5                   10                  15

Leu Val Thr Thr Ile Gly Leu Gly Val Arg Ala Ala
            20                  25
```

<210> SEQ ID NO 30
<211> LENGTH: 29
<212> TYPE: PRT
<213> ORGANISM: Modified Homo sapiens

<400> SEQUENCE: 30

```
Lys Lys Lys Lys Ala Ala Arg Val Gly Leu Gly Ile Thr Thr Val Leu
1               5                   10                  15

Leu Leu Val Thr Thr Ile Gly Leu Gly Val Arg Ala Ala
            20                  25
```

<210> SEQ ID NO 31
<211> LENGTH: 30
<212> TYPE: PRT
<213> ORGANISM: Modified Homo sapiens

<400> SEQUENCE: 31

```
Lys Lys Lys Lys Ala Ala Arg Val Gly Leu Gly Ile Thr Thr Val Leu
1               5                   10                  15

Leu Leu Leu Val Thr Thr Ile Gly Leu Gly Val Arg Ala Ala
            20                  25                  30
```

<210> SEQ ID NO 32
<211> LENGTH: 22
<212> TYPE: PRT
<213> ORGANISM: Modified Homo sapiens
<220> FEATURE:
<221> NAME/KEY: misc_feature
<222> LOCATION: ()..()
<223> OTHER INFORMATION: X is Di-aminopimelic acid

<400> SEQUENCE: 32

```
Lys Lys Lys Lys Pro Ala Arg Val Gly Leu Gly Ile Thr Thr Val Leu
1               5                   10                  15

Thr Arg Thr Thr Xaa Ser
            20
```

<210> SEQ ID NO 33
<211> LENGTH: 25
<212> TYPE: PRT
<213> ORGANISM: Modified Homo sapiens

<400> SEQUENCE: 33

```
Lys Lys Lys Lys Pro Ala Arg Val Gly Leu Gly Ile Thr Thr Val Leu
1               5                   10                  15

Thr Met Thr Thr Gln Ser Ser Gly Ser
            20                  25
```

<210> SEQ ID NO 34
<211> LENGTH: 22
<212> TYPE: PRT

-continued

<213> ORGANISM: Modified Homo sapiens

<400> SEQUENCE: 34

Lys Lys Lys Lys Pro Ala Arg Val Gly Leu Gly Ile Thr Thr Val Leu
1 5 10 15

Thr Met Thr Thr Gln Ser
20

<210> SEQ ID NO 35
<211> LENGTH: 21
<212> TYPE: PRT
<213> ORGANISM: Modified Homo sapiens

<400> SEQUENCE: 35

Lys Lys Lys Lys Pro Ala Arg Val Gly Leu Gly Ile Thr Thr Val Leu
1 5 10 15

Thr Met Thr Thr Gln
20

<210> SEQ ID NO 36
<211> LENGTH: 20
<212> TYPE: PRT
<213> ORGANISM: Modified Homo sapiens

<400> SEQUENCE: 36

Lys Lys Lys Lys Pro Ala Arg Val Gly Leu Gly Ile Thr Thr Val Leu
1 5 10 15

Thr Met Thr Thr
20

<210> SEQ ID NO 37
<211> LENGTH: 19
<212> TYPE: PRT
<213> ORGANISM: Modified Homo sapiens

<400> SEQUENCE: 37

Lys Lys Lys Lys Pro Ala Arg Val Gly Leu Gly Ile Thr Thr Val Leu
1 5 10 15

Thr Met Thr

<210> SEQ ID NO 38
<211> LENGTH: 18
<212> TYPE: PRT
<213> ORGANISM: Modified Homo sapiens

<400> SEQUENCE: 38

Lys Lys Lys Lys Pro Ala Arg Val Gly Leu Gly Ile Thr Thr Val Leu
1 5 10 15

Thr Met

<210> SEQ ID NO 39
<211> LENGTH: 17
<212> TYPE: PRT
<213> ORGANISM: Modified Homo sapiens

<400> SEQUENCE: 39

Lys Lys Lys Lys Pro Ala Arg Val Gly Leu Gly Ile Thr Thr Val Leu
1 5 10 15

Thr

<210> SEQ ID NO 40

-continued

<211> LENGTH: 16
<212> TYPE: PRT
<213> ORGANISM: Modified Homo sapiens

<400> SEQUENCE: 40

Lys Lys Lys Lys Pro Ala Arg Val Gly Leu Gly Ile Thr Thr Val Leu
1 5 10 15

<210> SEQ ID NO 41
<211> LENGTH: 25
<212> TYPE: PRT
<213> ORGANISM: Modified Homo sapiens

<400> SEQUENCE: 41

Arg Val Gly Leu Gly Ile Thr Thr Val Leu Thr Met Thr Thr Gln Ser
1 5 10 15

Ser Gly Ser Arg Ala Lys Lys Lys Lys
20 25

<210> SEQ ID NO 42
<211> LENGTH: 23
<212> TYPE: PRT
<213> ORGANISM: Modified Homo sapiens

<400> SEQUENCE: 42

Gly Leu Gly Ile Thr Thr Val Leu Thr Met Thr Thr Gln Ser Ser Gly
1 5 10 15

Ser Arg Ala Lys Lys Lys Lys
20

<210> SEQ ID NO 43
<211> LENGTH: 22
<212> TYPE: PRT
<213> ORGANISM: Modified Homo sapiens

<400> SEQUENCE: 43

Leu Gly Ile Thr Thr Val Leu Thr Met Thr Thr Gln Ser Ser Gly Ser
1 5 10 15

Arg Ala Lys Lys Lys Lys
20

<210> SEQ ID NO 44
<211> LENGTH: 21
<212> TYPE: PRT
<213> ORGANISM: Modified Homo sapiens

<400> SEQUENCE: 44

Gly Ile Thr Thr Val Leu Thr Met Thr Thr Gln Ser Ser Gly Ser Arg
1 5 10 15

Ala Lys Lys Lys Lys
20

<210> SEQ ID NO 45
<211> LENGTH: 20
<212> TYPE: PRT
<213> ORGANISM: Modified Homo sapiens

<400> SEQUENCE: 45

Ile Thr Thr Val Leu Thr Met Thr Thr Gln Ser Ser Gly Ser Arg Ala
1 5 10 15

Lys Lys Lys Lys
20

-continued

<210> SEQ ID NO 46
<211> LENGTH: 16
<212> TYPE: PRT
<213> ORGANISM: Modified Homo sapiens

<400> SEQUENCE: 46

Leu Thr Met Thr Thr Gln Ser Ser Gly Ser Arg Ala Lys Lys Lys Lys
1 5 10 15

<210> SEQ ID NO 47
<211> LENGTH: 31
<212> TYPE: PRT
<213> ORGANISM: Modified Homo sapiens

<400> SEQUENCE: 47

Lys Lys Lys Lys Pro Ala Arg Val Gly Leu Gly Ile Thr Thr Val Leu
1 5 10 15

Thr Met Thr Thr Gln Ser Ser Gly Ser Arg Ala Lys Lys Lys Lys
20 25 30

<210> SEQ ID NO 48
<211> LENGTH: 11
<212> TYPE: PRT
<213> ORGANISM: Modified Homo sapiens

<400> SEQUENCE: 48

Pro Ala Arg Val Gly Leu Gly Ile Thr Thr Val
1 5 10

<210> SEQ ID NO 49
<211> LENGTH: 11
<212> TYPE: PRT
<213> ORGANISM: Modified Homo sapiens

<400> SEQUENCE: 49

Thr Met Thr Thr Gln Ser Ser Gly Ser Arg Ala
1 5 10

<210> SEQ ID NO 50
<211> LENGTH: 11
<212> TYPE: PRT
<213> ORGANISM: Modified Homo sapiens

<400> SEQUENCE: 50

Val Thr Thr Ile Gly Leu Gly Val Arg Ala Pro
1 5 10

<210> SEQ ID NO 51
<211> LENGTH: 11
<212> TYPE: PRT
<213> ORGANISM: Modified Homo sapiens

<400> SEQUENCE: 51

Ala Arg Ser Gly Ser Ser Gln Thr Thr Met Thr
1 5 10

<210> SEQ ID NO 52
<211> LENGTH: 11
<212> TYPE: PRT
<213> ORGANISM: Modified Homo sapiens

<400> SEQUENCE: 52

Ala Ala Arg Val Gly Leu Gly Ile Thr Thr Val
1 5 10

-continued

```
<210> SEQ ID NO 53
<211> LENGTH: 11
<212> TYPE: PRT
<213> ORGANISM: Modified Homo sapiens

<400> SEQUENCE: 53

Val Thr Thr Ile Gly Leu Gly Val Arg Ala Ala
1               5                   10
```